(12) United States Patent
Heath

(10) Patent No.: US 11,298,551 B2
(45) Date of Patent: *Apr. 12, 2022

(54) SPHERICAL INPUT AND OUTPUT METHODS AND DEVICES

(71) Applicant: iOSphere Labs

(72) Inventor: Jason F Heath, Culver City, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 16/991,032

(22) Filed: Aug. 12, 2020

(65) Prior Publication Data

US 2020/0371622 A1   Nov. 26, 2020

Related U.S. Application Data

(63) Continuation of application No. 15/853,722, filed on Dec. 23, 2017, now Pat. No. 10,775,941.
(Continued)

(51) Int. Cl.
*G06F 3/044* (2006.01)
*A61N 1/372* (2006.01)
(Continued)

(52) U.S. Cl.
CPC ........ *A61N 1/37247* (2013.01); *A63B 43/004* (2013.01); *A63B 71/0622* (2013.01); *A63F 13/211* (2014.09); *G06F 1/16* (2013.01); *G06F 3/016* (2013.01); *G06F 3/02* (2013.01); *G06F 3/0202* (2013.01); *G06F 3/0219* (2013.01); *G06F 3/044* (2013.01); *G06F 3/0414* (2013.01); *G06F 3/04847* (2013.01); *G09B 5/06* (2013.01); *G09B 15/00* (2013.01); *G10H 1/0008* (2013.01); *G10H 1/0551* (2013.01);

*G10H 1/344* (2013.01); *A63B 2071/0625* (2013.01); *A63B 2220/30* (2013.01); *A63B 2220/56* (2013.01);
(Continued)

(58) Field of Classification Search
CPC .......... G06F 3/038; G06F 3/017; G06F 3/033; G06F 3/013; G06F 3/041; G06F 3/0416; G06F 3/044; G06F 3/0354; G06F 3/03545; G06F 3/016
See application file for complete search history.

(56) References Cited

U.S. PATENT DOCUMENTS 5,287,089 A    2/1994 Parsons
5,663,514 A *  9/1997 Usa .................... G10H 1/40
                                                    84/600
(Continued)

*Primary Examiner* — Olga V Merkoulova

(57) ABSTRACT

Described herein are embodiments of sensorized spherical input and output devices, systems, and methods for capturing gestural input from a user's physical interactions with a spherical device, including tossing, bouncing and spinning. In one embodiment, the spherical input and output device includes force sensors in a configuration to capture a variety of user gestures with the sphere. A microprocessor receives sensor input and transmits the sensor data to receiving devices which include computer software to translate the sensor signals to audio output, visual output, or various functions on receiving devices. Embodiments of the invention include the integration of inertial measurement units (IMUs), which may include a combination of accelerometers, gyroscopes and magnetometers to capture complex user gestures involving motion, direction and spin of the sensorized sphere in three dimensional space.

19 Claims, 18 Drawing Sheets

Related U.S. Application Data

(60) Provisional application No. 62/441,113, filed on Dec. 30, 2016.

(51) Int. Cl.

| | | |
|---|---|---|
| *G06F 3/01* | (2006.01) | |
| *G09B 5/06* | (2006.01) | |
| *A63B 43/00* | (2006.01) | |
| *A63F 13/211* | (2014.01) | |
| *A63B 71/06* | (2006.01) | |
| *G10H 1/00* | (2006.01) | |
| *G09B 15/00* | (2006.01) | |
| *G06F 3/04847* | (2022.01) | |
| *G10H 1/055* | (2006.01) | |
| *G06F 3/02* | (2006.01) | |
| *G10H 1/34* | (2006.01) | |
| *G06F 1/16* | (2006.01) | |
| *G06F 3/041* | (2006.01) | |
| *G10H 1/32* | (2006.01) | |

(52) U.S. Cl.
CPC ......... *G10H 1/32* (2013.01); *G10H 2220/116* (2013.01); *G10H 2220/155* (2013.01); *G10H 2220/391* (2013.01); *G10H 2220/395* (2013.01); *G10H 2240/211* (2013.01)

(56) References Cited

U.S. PATENT DOCUMENTS

| | | | |
|---|---|---|---|
| 5,666,473 A | 9/1997 | Wallace | |
| 5,923,318 A | 7/1999 | Zhai | |
| 6,184,454 B1* | 2/2001 | Imai | G10H 1/0066 84/622 |
| 6,891,527 B1 | 5/2005 | Chapman | |
| D543,212 S | 5/2007 | Marks | |
| 7,755,605 B2 | 7/2010 | Daniel | |
| 7,808,484 B1 | 10/2010 | Bareli | |
| 8,149,209 B1 | 4/2012 | Leebow | |
| 8,207,939 B1 | 6/2012 | Bareli | |
| D748,095 S * | 1/2016 | Oikawa | D14/408 |
| 9,474,968 B2 | 10/2016 | Zalewski | |
| 9,740,305 B2 | 8/2017 | Kabasawa | |
| 10,031,594 B2 | 7/2018 | Albano | |
| 10,180,731 B2 | 1/2019 | Clambaneva | |
| 10,748,437 B2* | 8/2020 | Lynch | G09B 5/00 |
| 10,775,941 B2* | 9/2020 | Heath | A63B 43/004 |
| 2002/0083425 A1 | 6/2002 | Gillies | |
| 2007/0211033 A1 | 9/2007 | Farag | |
| 2009/0040175 A1* | 2/2009 | Xu | G06F 3/0346 345/156 |
| 2009/0225030 A1 | 9/2009 | Vaananen | |
| 2011/0310002 A1* | 12/2011 | Tidemand | A63F 13/235 345/156 |
| 2012/0011932 A1* | 1/2012 | Nakagawa | G06F 3/0383 73/379.02 |
| 2012/0017702 A1 | 1/2012 | Kawabe | |
| 2012/0154387 A1* | 6/2012 | Tsukahara | G06F 3/0346 345/419 |
| 2012/0179408 A1* | 7/2012 | Goto | G06F 3/0346 702/104 |
| 2013/0027294 A1* | 1/2013 | Nakagawa | G06F 3/0346 345/156 |
| 2013/0088421 A1* | 4/2013 | Ueno | G06F 1/1694 345/156 |
| 2014/0201477 A1 | 7/2014 | Greenfield | |
| 2015/0042563 A1* | 2/2015 | Tsukahara | G06F 3/0346 345/157 |
| 2017/0031502 A1* | 2/2017 | Rosenberg | G06F 3/04144 |
| 2018/0188850 A1* | 7/2018 | Heath | A63B 71/0622 |

* cited by examiner

SPHERICAL INPUT AND OUTPUT METHODS AND DEVICES

PRIORITY

This U.S. non-provisional utility application is a continuation application of and claims priority to U.S. non-provisional application Ser. No. 15/853,722, filed Dec. 23, 2017 which claims priority to provisional application U.S. Application No. 62/441,113, filed Dec. 30, 2016.

FIELD

Aspects of the present disclosure relate to a sensorized spherical input and output device for systems, processes and applications for learning, music, rehabilitation and gaming.

BACKGROUND

A sphere is an object that is universally found in nature from planets, stars, to atomic particles. Because of its spherical qualities and interaction with forces such as gravity and movement in space, the ball has been an ideal object for sport and play that has spanned uses in civilizations from ancient to modern. A sphere's inherent qualities and unique interaction with forces in nature render it an ideal object for human use and interaction. And while balls and spheres have been ubiquitous in traditional sports and games, there are few devices in the market that combine the properties of a sphere to capture full ranges of human gestures, forces and interactions and provide unique output applications based on these unique gestural inputs. And while interactive hardware and connected smart devices have become an integral part of society, there are few devices in the market that can combine the sphere's natural ability to capture human gestures to render interactive output in the form of music, data, art, gaming and learning applications.

Moreover, there is need for spherical input and output devices in healthcare. Rehabilitation of stroke patients and other patients who have neuromuscular or neurodegenerative disorders with loss of motor or sensory functions requires treatment that includes motor and sensory learning. In patients with a neurodegenerative disorder (such as stroke) a person may lose fine-tuned motor skills in their hands or fingers or be unable to complete complex tasks which require fine motor coordination. Other patients who suffer neurodegenerative damage may lose visual, auditory, tactile or other sense impressions that are vital to daily life.

It has been well-documented that intensive and repetitive training of motor skills can be used to modify neural organization and recovery of functional motor skills. Schneider S, Münte T, Rodriguez-Fornells A, Sailer M, E A, *Music-Supported Training is More Efficient than Functional Motor Training for Recovery of Fine Motor Skills in Stroke Patients*. Music Perception: An Interdisciplinary Journal. 2010; 27(4):271-280. doi:10.1525/mp.2010.27.4.271. There are many forms of treatments currently being deployed for such patients, which include having patients squeeze objects, place blocks or objects in a puzzle, and even interact with computerized boards on a wall which been sensorized to detect whether a user has pushed a button in response to visual or auditory feedback. Other brain-training exercises include having a user play learning or memory games on a computer with a traditional mouse and keyboard which requires the user to identify objects or words on a screen and take appropriate responsive action in the game with the mouse or keyboard.

It has also been demonstrated that music and sound are beneficial to patients who have suffered neurodegenerative loss of motor or sensory skills. It is well documented that certain musical tones, timbres and rhythms can stimulate different parts of the brain, such as the auditory, visual occipital lobes, and also the cerebellum, motor cortex and amygdala. The complex range of musical tones, timbres, and rhythms can activate different regions of the brain and trigger neurophysiological responses and cognitive learning. Studies have shown that music improves learning and cognitive functions in patients with cognitive or neurodegenerative disorders. Brain mapping studies have shown a clear correlation between musical notes, tones, frequencies, tempo, rhythm and other musical intonations which correspond to different regions or interactions of different regions within the brain. Gaidos S., *More than a feeling: Emotionally evocative, yes, but music goes much deeper*. Science News. 2010; 178(4):24-29. doi:10.1002/scin.5591780423.

The auditory cortex is organized in terms of sound frequencies, with some cells responding to low frequencies and others to high. Moving from the inside to the outside of part of the auditory cortex, different kinds of auditory analysis take place. In the core, basic musical elements, such as pitch and volume, are analyzed, whereas surrounding regions process more complex elements, such as timbre, melody and rhythm.

There are few activities that require more of the brain than playing music. It uses complex feedback systems that take in information, such as pitch and melody, through the auditory cortex and allow the performer to adjust their playing.

The visual cortex is activated by reading or even imagining a score; the parietal lobe is involved in a number of processes, including computation of finger position; the motor cortex helps control body movements; the sensory cortex is stimulated with each touch of the instrument; the premotor area helps perform movements in the correct order and time; the frontal lobe plans and coordinates the overall activity; and the cerebellum helps create smooth, integrated movements. Habib M, Besson M., *What do Music Training and Musical Experience Teach Us About Brain Plasticity?* Music Perception: An Interdisciplinary Journal. 2009; 26(3): 279-285. doi:10.1525/mp.2009.26.3.279.

It is also well documented that musical learning helps autistic children and children with learning disorders. Research shows that music enhances and optimizes the brain, providing better, more efficient therapy and improved performance of cognitive, motor, and speech/language tasks. Lee H, Noppeney U., *Long-term music training tunes how the brain temporally binds signals from multiple senses*. Proceedings of the National Academy of Sciences. 2011; 108(51). doi:10.1073/pnas.1115267108. Studies show that people perform these tasks better with music than without.

Research shows musical training in children enhances the activity of important neural systems. Playing a musical instrument results in changes in the brain in specific regions such as the auditory cortex used for processing musical tones; the motor cortex, a region activated when using the hands or fingers; the cerebellum, a part of the brain used in timing and learning; and the corpus callosum, which acts as a bridge between both hemispheres of the brain. Other regions may also be enhanced.

Studies show that music can improve motor skills. Palmer C, Meyer R K., *Conceptual and Motor Learning in Music Performance*. Psychological Science. 2000; 11(1):63-68. doi:10.1111/1467-9280.00216. Research supports parallels between rhythm and movement. Rhythm can be used as an external timekeeper to organize, coordinate, and improve movement. Halsband U, Binkofski F, Camp M. *The Role of the Perception of Rhythmic Grouping in Musical Performance: Evidence from Motor-Skill Development in Piano Playing*. Music Perception: An Interdisciplinary Journal. 1994; 11(3):265-288. doi:10.2307/40285623. Musical training and engagement can facilitate more functional, organized, coordinated, and higher quality movements in fine motor and gross motor skills including motor planning, motor control, motor coordination, gait training and body awareness.

Research also demonstrates that music can improve cognitive skills. Music provides an optimal learning environment, organizes information into smaller packages that are easier to learn and retain, and aids in memorization. Music has the capacity to engage attention and encourage concentration. Research indicates that attention is necessary before learning can take place. Research indicates that music is often successful as a mnemonic device for learning new concepts, such as learning the alphabet through the "ABC Song". Music therapists use music to improve cognitive skills such as attention, memory, mood, and executive functioning (higher level thought processing), including academic skills. *Making Material More Memorable . . . with Music*. The American Biology Teacher. 2013; 75(9):713-714. doi:10.1525/abt.2013.75.9.16.

Musical learning can improve speech and language. Research supports parallels between singing and speech production, and music's ability to facilitate improved communication skills. Murphy A T, Simons R F., *Music Therapy for the Speech-Handicapped*. The Elementary School Journal. 1958; 59(1):39-45. doi:10.1086/459687. Musical engagement can enable those without language to communicate and express themselves non-verbally. Additionally, musical engagement often assists in the development of verbal communication, speech, and language skills. Music therapists can assist a person with dysfunction or delays in various speech/language abilities to learn how to speak through singing or communicate nonverbally through music.

Music can also improve social, emotional and behavioral skills. Music is highly motivating and engaging and may be used as a natural reinforcer for desired responses. Musical engagement can stimulate patients to reduce negative and/or self-stimulatory responses and increase participation in more socially appropriate ways. Musical engagement facilitates improved social skills such as shared play, turn-taking, reciprocity, and listening and responding to others. Musical engagement also provides a non-threatening and structured environment in which individuals have the opportunity to develop identification and appropriate expression of their emotions.

Music can improve sensory skills. Music provides concrete, multi-sensory stimulation (auditory, visual, and tactile). The rhythmic component of music is very organizing for the sensory systems, and as a result, auditory, visual, tactile, proprioceptive (input to muscles and joints), vestibular (input for balance) and self-regulation processing skills can be improved through musical engagement.

Since it has been shown that patients with neurodegenerative, sensory, motor or cognitive disorders react favorably to games and interactive devices, a sensorized ball or sphere is an ideal object for patients: it can be easily adaptable to therapies that enhance learning and benefit from dynamic interactions. A ball, which is spherical in shape, can be easily held, rolled, touched and squeezed. Such a ball can be adapted with a number of different sensors that measure data related to touch or movement, and can be mapped to generate auditory, visual, and haptic feedback for the user. A ball that has sensors and an embedded processor can record the input of the user or patient as they interact with the ball through pressing sensors, rolling, or throwing and catching the object. Interaction with such a ball can stimulate learning, improved motor function and sensory stimulation, as well as neurophysiological changes which can be recorded through software, hardware and brain mapping tools such as CAT, PET, EEG or MM scanning equipment.

In order to track the motor developmental progress of stroke patients, and others with neuro-motor, neuro-sensory, or neurodegenerative disorders, what is desired is a sensorized ball that is connected to a computer which records user input (in the form of pressure, touch, movement, and other gestures) and has output means to provide a visual display and auditory feedback of the user's interactions with the ball.

Also provided the documented benefits of neuro-musical therapy, what is needed is a ball that adapts as a musical instrument based on the abilities and skills of a user. For example, facilitating a meaningful musical experience for a patient with neurodegenerative impairments using a traditional keyboard, trumpet or even a computer, under the theory that music learning and engagement enhances general learning and cognitive function, can present prohibitive barriers for a therapist and their patient. Such instruments are difficult to learn even for patients without motor, sensory or cognitive impairments. However, a ball that simply requires the user to squeeze one or more areas activated by sensors that fit the natural gestures of a user is far more approachable for a user with neurodegenerative and/or cognitive issues. Such a ball can be programmed based on the input and abilities of the user, unlike traditional musical instruments.

Another benefit of such a device is to introduce a variety of musical possibilities that can be customized by a user through a computer user interface. This allows a user to selectively specify the sounds, instruments, and audio samples which are mapped to one or more sensors along the surface area of a sensorized spherical device.

SUMMARY OF PREFERRED EMBODIMENTS OF THE INVENTION

Figure 1:
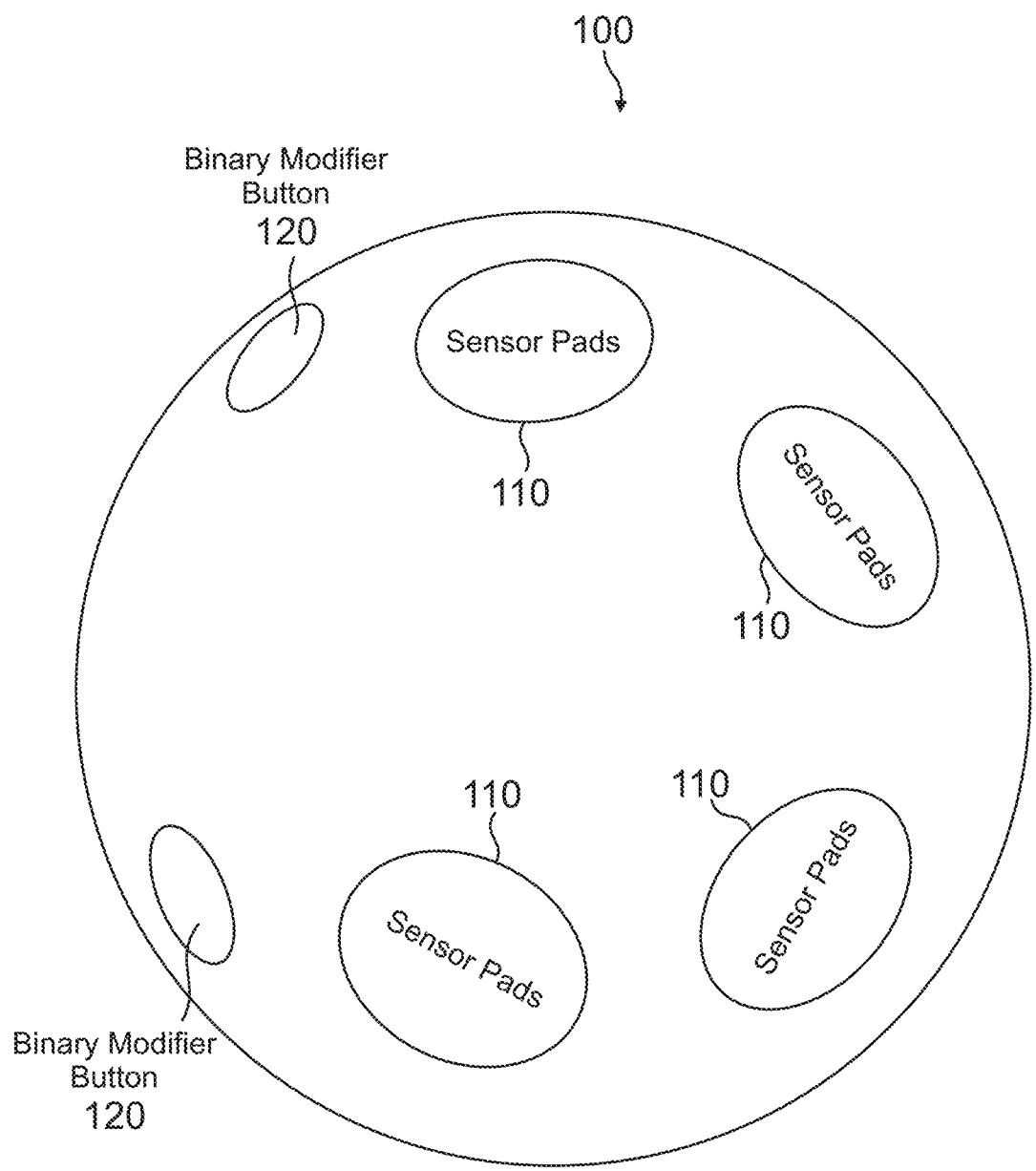
FIG. 1 is a diagram conceptually illustrating a sensorized sphere in one embodiment.

An embodiment of the present invention is a sensorized spherical control interface, and input and output device capable of sending and receiving user-input data wirelessly to and from other devices, which can then be mapped to control music and sound, video, lights, motors, video game mechanics, and other systems; as well as can be used to capture and record data streams from user input. In one embodiment, sensors are embedded along the surface of the sphere allowing it to maintain the physical properties of a sphere. The sensorized spherical interface can be used for medical rehabilitation therapies; as a musical instrument; for dancers and other artists; in a series of learning games for children; in sporting goods; to control video game mechanics; in robotics; and generally as a more ergonomic input/output device for interfacing with a wide variety of other systems.

One embodiment of the invention includes a spherical input and output device with sensors responsive to input from a plurality of user gestures; wherein a plurality of sensors are in a spatial proximity along the surface area of said spherical input and output device in a configuration capable of receiving input from the hands and fingers of a user grasping the spherical input and output device with one or both hands; an inner core with electrical components comprising: a microprocessor for processing signals from one or more said sensors; a power source for powering said sensors and said electrical components; a transceiver for transmitting sensor signals corresponding to said plurality of user gestures to a computing device.

One embodiment of the invention includes a method for capturing electrical input from a spherical input and output device, including the steps of: receiving input through sensors from a plurality of user gestures; wherein the plurality of the sensors are in spatial proximity along the surface area of the spherical input and output device in a configuration capable of receiving input from the hands and fingers of a user grasping the spherical input and output device with one or both hands; receiving electrical signals at a microprocessor from a plurality of sensors responsive to each of said plurality of user gestures; processing said electrical signals to create a data output corresponding to each of said plurality of user gestures; and transmitting the data output to a computing device.

One embodiment of the invention includes a sensorized sphere wherein a plurality of sensors capture user gestures through a sensing module responsive to touch, a sensing module responsive to force, and a sensing module responsive to movement or orientation of the device.

In one embodiment, the sensors are selected from a group consisting of tactile sensors, force sensors, pressure sensors, proximity sensors, and inertial measurement units (IMU) including, accelerometers, magnetometers, and gyroscopes.

In one embodiment, the sensorized sphere comprises one or more capacitive sensors or sensor arrays for capturing data from a plurality of user gestures.

In some embodiments, the sensorized sphere includes an outer protective material made of rubber, silicone, plastic, glass, wood, fabric, or a synthetic polymer.

In one embodiment, the inner core of the sensorized sphere is surrounded by a first conductive layer, second resistive layer, and third conductive layer.

In one embodiment, the sensorized sphere has force sensors inlaid under an outer layer in a configuration to conform to a plurality of fingers from a human hand such that when the the device is grasped by the user, the sensors are in proximity to a plurality of fingers.

In one embodiment, the sensorized sphere is electrically coupled to a computing device which may include a smartphone, tablet computer, audio output system, television, laptop, desktop computer, MRI machine, EEG machine and other medical devices which are capable of providing real time feedback on a user's neuronal activity.

One embodiment of the invention is a system for processing sensor signals from a spherical input and output device, including: a computing device electrically coupled to the spherical input and output device; a receiver for receiving signals from the sensors of the spherical input and output device; a sensor processing engine for processing the sensor signals; a memory for storing data corresponding to sensor inputs; an audio engine for translating the sensor signals to audio outputs corresponding to said data; and a graphics engine for displaying the data files corresponding to the sensor output signals.

One embodiment of the system includes audio files individually mapped to individual sensors on the spherical input and output device; wherein the audio output can be modified based on the user's gestures with said spherical input and output device to create a multilayered musical experience.

One embodiment of the system includes computer programmable code for generating a map, or graph, and a data history of the user's gestures with the spherical input and output device to track the progress and motor mobility of a user's hands and individual fingers.

One embodiment of the system includes a haptics module for providing tactile feedback to the user based on the user's gestures with the spherical input and output device.

One embodiment of the invention is approximately 5-7 inches in diameter and includes a protective spherical core and a shell (with a skin) which covers the core. The core contains a circuit board, a microprocessor, an accelerometer, a gyroscope, a wireless transmitter, and a battery. The shell contains an array of sensors which are embedded and inlaid into the surface (skin) of the sphere and that connect to processors in the circuit board inside the protective core. In one embodiment, the shell and skin are replaceable and interchangeable as accessories, according to different uses and software mappings.

One embodiment of the invention includes a metal core covered by a resistive fabric material, and a conductive silicone (or conductive rubber) shell and skin. When the user squeezes the sphere, the resistance measured between the metal core and the conductive shell decreases. These fluctuations in measured resistance can be used to measure the user's force on the sphere, and can be mapped to musical gestures such as swelling dynamics in sample playback, or to trigger musical events according to different degree-stages of force.

One embodiment of the invention includes small silicone force-sensing buttons which are seamlessly inlaid into the surface skin of the sphere in an array that allows for ergonomic use by following the natural positioning and contours of human hands as they naturally and comfortably rest on the surface of the sphere.

One embodiment of the invention includes proximity sensors embedded in the surface of the sphere to measure the user's hands' proximity to the surface of the sphere.

One embodiment of the invention includes fabric force sensors arranged ergonomically around the surface of the sphere.

One embodiment of the invention includes small sensors that are arranged in an array covering the entire surface area of the sphere.

One embodiment of the invention includes an augmented reality engine which can dynamically remap the user interface configuration.

One embodiment of the invention includes a wooden shell and skin, with built-in capacitive touch sensors.

One embodiment of the invention includes a glass shell and skin, with built-in capacitive touch sensors.

One embodiment of the invention includes a metal shell and skin, with built-in capacitive touch sensors.

One embodiment of the invention includes linear potentiometer sensors embedded in the surface of the sphere that measure the distance (along a slider) from the surface of the sphere as the user applies force towards the sphere's core. The linear potentiometer extends from the surface of the sphere into its shell and is also fixed to the core at its other end. At the top of the potentiometer is a small button which is fused flush with the surface of the skin. The slider is moved up as the user applies force to the button fused into the surface of the sphere's material, and down as the material recovers from the force. The amount of force required to move the potentiometer is therefore determined by the properties of each uniquely chosen shell and skin materials. A soft silicone shell will require less force than a very hard rubber shell, for example. Also, as different materials recover their form very differently after force has been applied, the materials chosen in each case will affect the recovery of the potentiometer to its resting position. These sensors are very cost-effective and can provide a rich amount of data. The integrated sensors' range will also be affected by the nature of the materials used for the shell and skin.

One embodiment of the invention includes light sensors that orient outwards from the core through holes in the surface of the sphere. These holes are covered by a clear membrane so as to allow light through while also maintaining a seamless surface and skin. As the user covers and uncovers specific holes, data is sent to a microprocessor and corresponding software mapping on a computing device.

One embodiment of the invention includes a charging station with built-in speakers and embedded system, including a CPU and touchscreen. The sphere is wirelessly paired with the docking station and runs the various software systems for each different mapping of the sphere's data stream.

One embodiment of the invention includes a camera (or series of cameras) which can be employed as sensors or as live video feed affected by gestures and other user controls.

One embodiment of the software mapping is to control the spatial position, direction, and speed of musical sounds and other sound design.

One embodiment of the software mapping is to control the spatial position, direction, and speed of a physical drone, or other similar remote-controlled devices and uncrewed vehicles.

DETAILED DESCRIPTION

One embodiment of the software mapping is to control the spatial position, direction, and speed of a physical drone, or other similar remote-controlled devices and uncrewed vehicles.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, and in order to avoid obscuring such concepts, well-known structures and components are shown in block diagram form.

One embodiment of the invention includes ten sensors embedded along the surface the sphere. In one embodiment, the sphere is approximately 5-7 inches in diameter in order to conform to the shape of an average human hand and to allow a user to easily grasp the sphere with one or both hands. Sensors may be inside or outside of the surface. Each sensor position corresponds to one of the fingers of a human hand. In one prototype embodiment, force-sensing resistors (FSR) (0.5"), Sparkfun SEN-09375 ROHS made by Interlink Electronics were used. The properties and characteristics of these FSRs as described in *FSR Integration Guide and Evaluation Parts Catalog With Suggested Electrical Interfaces* (v.1.0, 90-45632 Rev. D), are incorporated by reference. This is a force sensitive resistor with a round, 0.5" diameter, sensing area. This FSR will vary its resistance depending on how much pressure is being applied to the sensing area. The harder the force, the lower the resistance. When no pressure is being applied to the FSR its resistance will be larger than 1 MΩ. This FSR can sense applied force anywhere in the range of 100 g-10 kg. These sensors can be placed at different regions along the sphere or core to allow for a natural grip by the user to optimally capture user gestures and interactions with the sphere. There is no limit on the number of sensors that can be embedded along the surface of the sphere. Along the surface may mean that some sensors may be inside the sphere with a distance in proximity to the surface, while others can be on the outside of the surface or just underneath a sensor pad. In one embodiment, the sensors may include force sensors which are triggered by the user's compression of the sensor or squeezing of the palms. Other types of sensors, including sensor arrays and matrices, tactile sensors and arrays (as well as piezoelectric, piezoresistive, capacitive, elastoresistive sensing) may also be employed, depending on the input that needs to be measured and in consideration of desirable outputs. The different types of sensors that can be used in the construction of the sensorized sphere are known to one of ordinary skill in the art. In one embodiment, a tactile matrix array is formed across the full inner surface of the sphere such that the user can hold or grip the ball from any direction and their fingertips will land on at least one tactile element.

In one embodiment, the force sensors in an array along the surface of the sphere are embedded into a compressive material (such as silicone or a foam, like blown EVA, for example) such that their behavior and data output is dependent on the materiality of the compressive layer as it relates to the positioning within said layer, of each of the sensors (FSR's, piezoresistive, or otherwise). A firmer, less compressive layer (with embedded sensors) will result in different sensor behavior and data output than a softer, more compressive layer; such that the sensors embedded in the more compressive layer will more slowly return to their default state of electrical resistance when engaged and then disengaged by a user, and likewise will be slightly slower and more measured in their response to being 'attacked' or compressed. A more compressive layer also potentially allows for a wider range of sensor sensitivity to certain gestures, and often a more steady, smoother data stream. There is an optimal range of material compression (according to each application and use case) as related to the embedded sensors, wherein the relationship affects the sensor behavior and the quality of data output, and in turn the possibilities for mapping user gestures to meaningful outputs. If the compressive layer is too soft, for example, it may affect the discreet data localization coming from each individual sensor as the shape of the surface becomes excessively distorted through user compression. If it is too firm, the user may lose some expressive controls and it may limit the range of effective user gestures and therefore limit the richness and diversity of applications.

The sensor signals are picked up at the core microprocessor. In one prototype embodiment, Development Board (central processor) Sparkfun Fio v3-ATmega32U4 DEV-11520 ROHS is used is used as the core microprocessor. The JST-connector and 3.3 v system voltage makes this processor suitable for portable devices. The processor is compatible with a Li-Poly battery (or lithium ion batteries). Wireless sensor networks and communications are provided by on-board XBee socket. The ATmega32U4, running at 8 MHz, makes it possible to use the on-board USB jack not only to charge a connected Li-Poly battery, but to program the device as well. The features and properties of this part as noted in the schematics and datasheets for Fio v3-ATmega32U4 are incorporated by reference herein. https://www.sparkfun.com/products/11520.

In one prototype embodiment, the microprocessor is connected to a wireless Bluetooth transmitter Bluetooth Module Sparkfun RN42-XV, WRL-11601 ROHS. The RN42XV is a small form factor, low power Bluetooth radio module offering plug-in compatibility for the widely used 2×10 (2 mm) socket typically used for 802.15.4 radio modules. Based on the 2×10 (2 mm) socket footprint often found in embedded applications, the Roving Networks' RN42XV module provides Bluetooth connectivity in legacy and existing designs that may have been based upon the 802.15.4 standard. The RN42XV Class 2 Bluetooth module is based on the RN42. This module supports multiple interface protocols, on-chip antenna and support for Bluetooth EDR. The RN42 delivers up to a 3 Mbps data rate for distances up to 20 meters. The properties and characteristics of this Bluetooth module as described in its datasheet RN4142XV-DS by Roving Networks (v.1.0) are incorporated by reference herein.

In one prototype embodiment, the microprocessor is further connected to an Inertial Measurement Unit (IMU) comprising an accelerometer, magnetometer, and gyroscope Adafruit 9-DOF LSM9DS0 chip. The chip is 33 mm×20 mm×2 mm/1.30"×0.79"×0.08" and weighs approximately 2.3 g. Inside the chip are three sensors, one is a 3-axis accelerometer, which can inform the user which direction is down towards the Earth (by measuring gravity) or how fast the board is accelerating in 3D space. The other is a 3-axis magnetometer that can sense where the strongest magnetic force is coming from, generally used to detect magnetic north. The third is a 3-axis gyroscope that can measure spin and twist. By combining this data a user can orient the sphere in 3D and use the unique gestural measurements of direction, acceleration, position and spin to uniquely manipulate the output of sound, music, mathematical or visual data and also calibrate the sphere. The properties and characteristics of this IMU are described in the datasheet for Adafruit 9-DOF Accel/Mag/Gyro+Temp Breakout Board—LSM9DS0, PRODUCT ID: 2021, which is incorporated by reference herein.

In one prototype embodiment, the microprocessor is further connected to a vibration motor, Sparkfun Vibration Motor ROB-08449 ROHS. The vibration motor provides haptic feedback to the user when one or more sensors are activated. The properties and characteristics of this vibration motor as described in Product Specification by Zhejiang Yuesui Electron Stock Co., Ltd., Model B1034.FL45-00-015 (2016 Jan. 12) is incorporated herein by reference.

In one prototype embodiment, the power source for the microprocessor, Bluetooth module, sensors and haptics is powered by Sparkfun Lithium-Ion 2 Ah, 3.7V at 2000 mAh, PRT-13855 ROHS. The battery is light-weight based on Lithium Ion chemistry and each cell outputs a nominal 3.7V at 2000 mAh and comes terminated with a standard 2-pin JST-PH connector. The properties and characteristics of this battery as described in Sparkfun datasheets and specifications at https://www.sparkfun.com/products/13855, is incorporated by reference herein.

In one embodiment, radio frequency signals from the Bluetooth module or other appropriate RF transmitting device are outputted to wireless receiver or transceiver of a computer, smartphone or tablet where the signals are further processed by the Central Processing Unit (CPU) and software that is resident on the user's computing device. The signal output may be translated by the computer's software system into musical notes, pre-programmed sounds, or melodies, colors, shapes, graphs, or any other logical output that corresponds to the sensory input from the sphere. The accelerometer/magnetometer/gyroscope, in combination or individually, may change the octave, frequency or amplitude of the note or audio data file that is mapped to each sensor, thereby allowing the user to use a single sensor to create a multitude of sounds, musical effects or visual outputs, including digital drawings.

In one embodiment, the shell body of the sensorized sphere consists of foam, and the core and its constituent processors are protected by a plastic inner ball or other suitable material which keeps the components safe and damage free. The core may also be made of solid rubber, silicone, 3D-printable materials, or any other suitable material that keeps the hardware of the sphere intact and safe from damage. Because the sensorized sphere may be thrown, dropped, tossed, or squeezed, the sphere is designed to contain and protect the core electronics from damage due to movement and/or impact; as well as to maintain their fixed positioning inside the sphere.

FIG. 1 depicts one embodiment of the sensorized sphere 100. The sensorized sphere is shown with sensor pads 110 which correspond to the placement of individual sensors 410 (see FIGS. 4 and 5) that are embedded on top of, or underneath the surface of the sensor pads 110. In one embodiment, the sensor pads 110 may be concave or convex and can receive tactile feedback of pressure, touch, force, or may be sensitive to changes in temperature or electromagnetism. In one embodiment, sensor pads 110 may be mechanical push buttons that receive feedback from the user of the sensorized sphere and complete the circuit to activate one or more sensors. Sensor pads 110 may consist of the same material as the outer surface 310 of the sensorized sphere, but may also be of another material. A different material may be used for the sensor pads to allow the user to find the sensor locations through touching the surface of the sphere, which can have significant implications for blind patients. In one embodiment, the sensorized sphere includes binary modifier buttons 120 (also referred to as binary modifiers 120) which may be in the form of mechanical binary push buttons as known to one of ordinary skill in the art. The binary modifier buttons may lie on top of, or underneath the surface of the sensorized sphere. In one embodiment, the binary modifier, sometimes also referred to the as the output modifier, may change the audio or visual sample that correspond to the data file of the individual sensors. In one embodiment, the binary modifier 120 can also be used for other features such as volume or to modify the output signal from sensors 410. The binary modifiers may change parameters such as speed or frequency of playback of audio or data files that correspond to individual sensors 410 of the sensorized sphere 100. The binary modifier 120 may also activate or deactivate different types of sensors, which measure touch, pressure, temperature, speed, acceleration, tilt, spin, gravity, magnetism, or any other type of suitable sensor that is integrated into the sensorized sphere. In this way, the binary modifier 120 may create different permutations of sensor use, activation, feedback and control of the sensors including modifying the signal output of the sensors 410. Sensor pads 110 may cover the entire or partial surface of the sensorized sphere 100.

Figure 2:
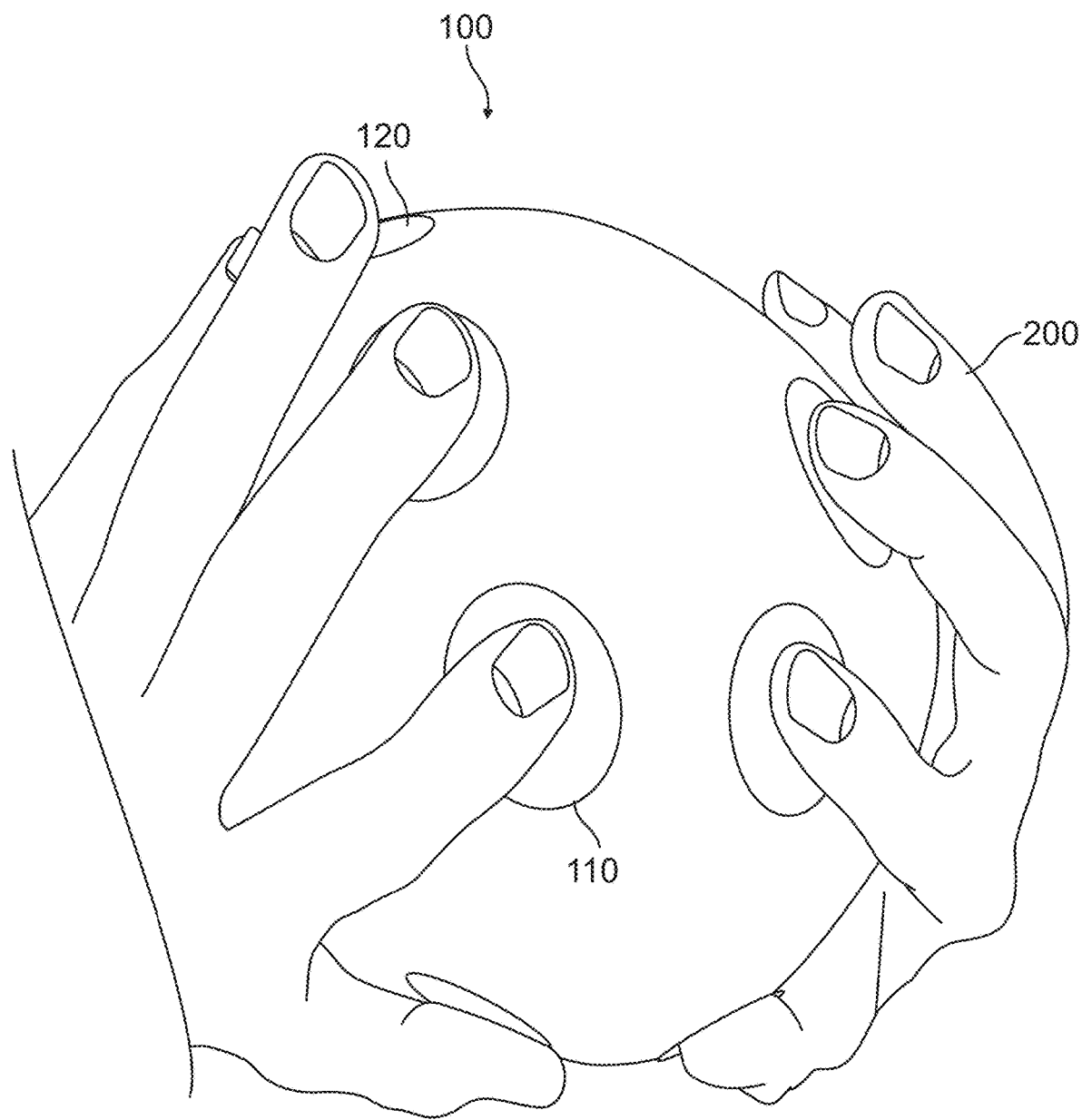
FIG. 2 is a diagram conceptually illustrating a user application of the sensorized sphere in one embodiment.

FIG. 2 depicts user interactions with a sensorized sphere according to one embodiment of the invention. As shown, sensorized sphere 100 can be easily gripped and handled by a user wherein his fingers may be conveniently placed on top of each of the sensor pads 110 and binary modifier buttons 120. In this way, according to one embodiment, the sensorized sphere can record the input of a user who may be using the sphere as a musical instrument (with each sensor corresponding to a different musical note or audio file), as the user touches or depresses each of the sensor pads 110 and their corresponding sensors 410. Using another finger on the binary modifier 120, the user may be able to change the configuration or output of each of the sensors 110. For example, in one embodiment, the binary modifier 120 may change the audio file that is linked to each of the sensors 410. The user can depress the binary modifier 120 and change one of several outputs corresponding to individual sensors 410. If there are three sensors pads 110 for each hand, as shown in this particular embodiment, each of the individual data files corresponding to that sensor can be changed, synchronized or harmonized with the audio outputs of the different sensors 410, thereby creating a unique musical instrument that is easily adapted to a user's needs. In one embodiment, the binary modifier 120 may activate or deactivate certain sensors depending on the type of input the user desires to record. For example, if the sensor pads 110 and sensors 410 are able to capture force and touch, and the user desires to obtain feedback on a patient's ability to use his fingers in recovery from stroke or another neurological condition, the binary modifier 120 may be configured to change the sensitivity or function of the various sensors 410 in order to optimally recover data from the patient. The binary modifiers 120 may also act as "On" and "Off" switches, turn on LED lights, Bluetooth connections, and serve any number of other functions. In some embodiments, the binary modifiers 120 are eliminated altogether and such functions are adopted by the sensors themselves.

Figure 3:
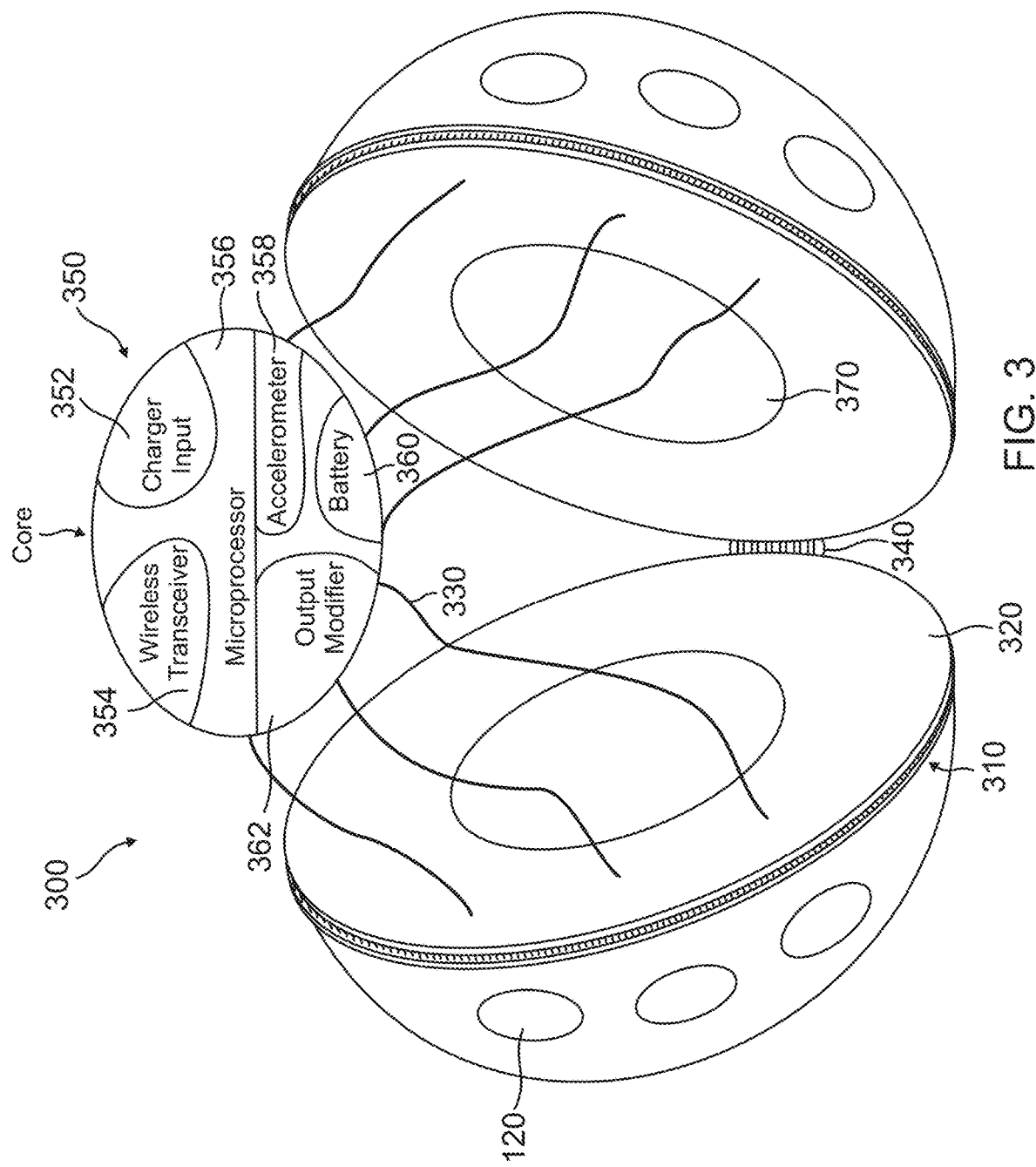
FIG. 3 is a diagram conceptually illustrating an embodiment of a sensorized sphere with its inner core and hardware displayed.

FIG. 3 depicts a cross-sectional view of a sensorized sphere 300 according to one embodiment of the invention. As shown, the sphere includes a core 350 which includes the hardware and electrical components of the sphere 300. The core 350 hardware components are connected to each of the individual sensors 410 and output modifiers 120. In one embodiment, the core 350 fits into an inner shell 370 which is hollow in the first core layer 320. The inner shell may be circular or any other shape that is suitable to encase the core 350. The sensorized sphere's outer surface 310 may be made of any different number of materials, including but not limited to rubber, silicone, plastic, fabric, foam, glass, wood, or any other suitable surface material which allows the sphere to maintain its circular and spherical shape, while allowing the integration and embedding of sensors along the surface area of the sphere. This may include embedding the sensors either inside or outside the sphere's outer surface 310.

In one embodiment, the sensorized sphere 300 also includes a first inner core 320 which encapsulates the components of core 350. The core 320 may be made out of foam, Styrofoam, rubber, silicone, plastic, or any other suitable materials that can provide the sphere its shape while serving as a protective layer for the inner core 350 components. In one embodiment, the sensorized sphere 300 can be opened through connector 310 which may include a zipper, or in other embodiments, a thread and screw twist-off mechanism which allows the user to open the sphere and reveal its two hemispheres. As shown here, in this embodiment, the two hemispheres of the sensorized sphere 300 are connected by hinge 340 and connector 310 which allows the sphere to be easily opened in order to change the battery 360, replace sensors 410, or access the processors, hardware, and firmware of core 350.

In one embodiment, of FIG. 3, as shown here, the sphere 300 contains a core 350 which is connected by electrical connectors 330 to each of the sensors 410 and binary modifiers 120. The connectors may include wired or wireless components for communicating signals with each of the sensors 410 and binary modifiers 120. The core 350 includes a charger input circuit 352, microprocessor 356, wireless transmitter or transceiver 354, accelerometer 358, battery 360 and output modifier processor 362.

Figure 6:
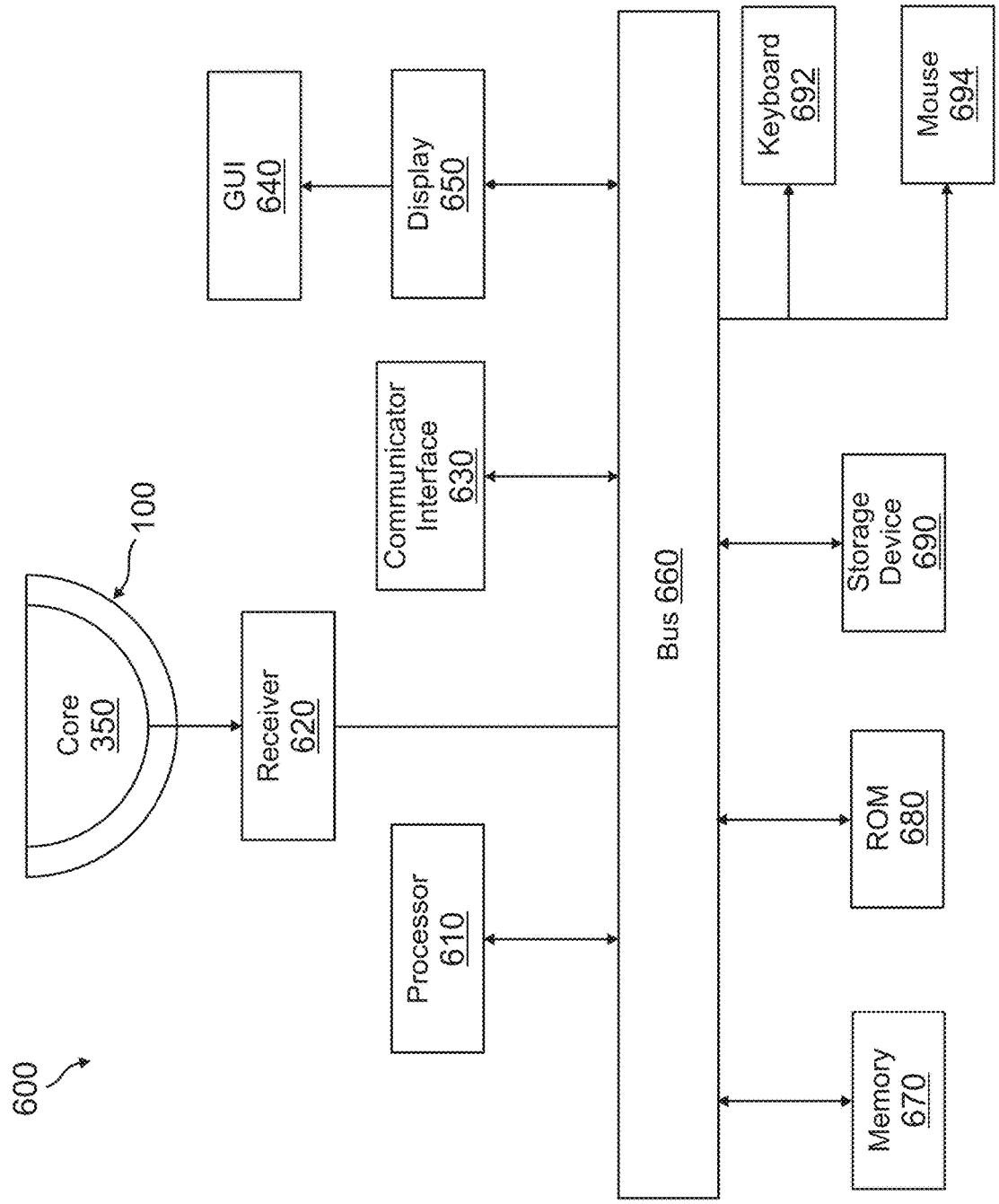
FIG. 6 is a diagram illustrating the connection of a remote user computer with the core of a sensorized sphere according to one embodiment.

In one embodiment, the inner core 320 of the sphere includes one or more sensors which react to a user's touch, compression, or other gestures of the user. As discussed herein, sensors along the surface, may be inside the core a suitable distance from the surface to detect changes in force, pressure, or resistance; and located just underneath the surface of the sensor pads 110, or on top of the surface of the sphere. The outer surface of the sphere may also include a USB port which can be used to charge the battery 360 inside the core. The battery is necessary to power the sensors, microprocessor, accelerometer, gyroscope, magnetometer, haptics, and any other electrical components of the sphere. The battery 360 may be a chargeable lithium ion or lithium polymer battery, or may consist of non-chargeable standard batteries which may be replaced by the user. The USB charging port is not shown here, but may reside inside the inner core 320 and accessible to a user on the outer surface 310. The USB charging port may also serve as a connector to a remote computer for uploading data to a user computer as shown in FIG. 6, or for downloading data to a storage device inside the core. The storage device may be any suitable computing memory device known to one of ordinary skill in the art. In one embodiment a sensorized sphere also contains an embedded wireless-charging technology that may use induction (such as the Qi open interface standard for wireless power transfer, or the PMA standard); magnetic resonance; RF energy; or any other available wireless charging, or power-transfer technology known to one of ordinary skill in the art. An induction system may be embedded in both the sensorized sphere and a docking station to charge when the sphere is docked and not in use. Alternatively, magnetic resonance or RF energy-based solutions may allow for enough power transfer over distance for a user to charge and/or power the device while it is in charging range of an enabled dock and power station.

In one embodiment, the microprocessor 356 processes signals from the sensors 410, the accelerometer 358 and output modifier 362 circuit. The output modifier circuit 362 is electrically connected to the binary modifiers 120. In one embodiment, the data signals from sensors 410 are processed at microprocessor 356 and relayed to a remote computer through the wireless transceiver 354. The electrical connection of the core 350 to a user's computing device is shown in FIG. 6.

Figure 4:
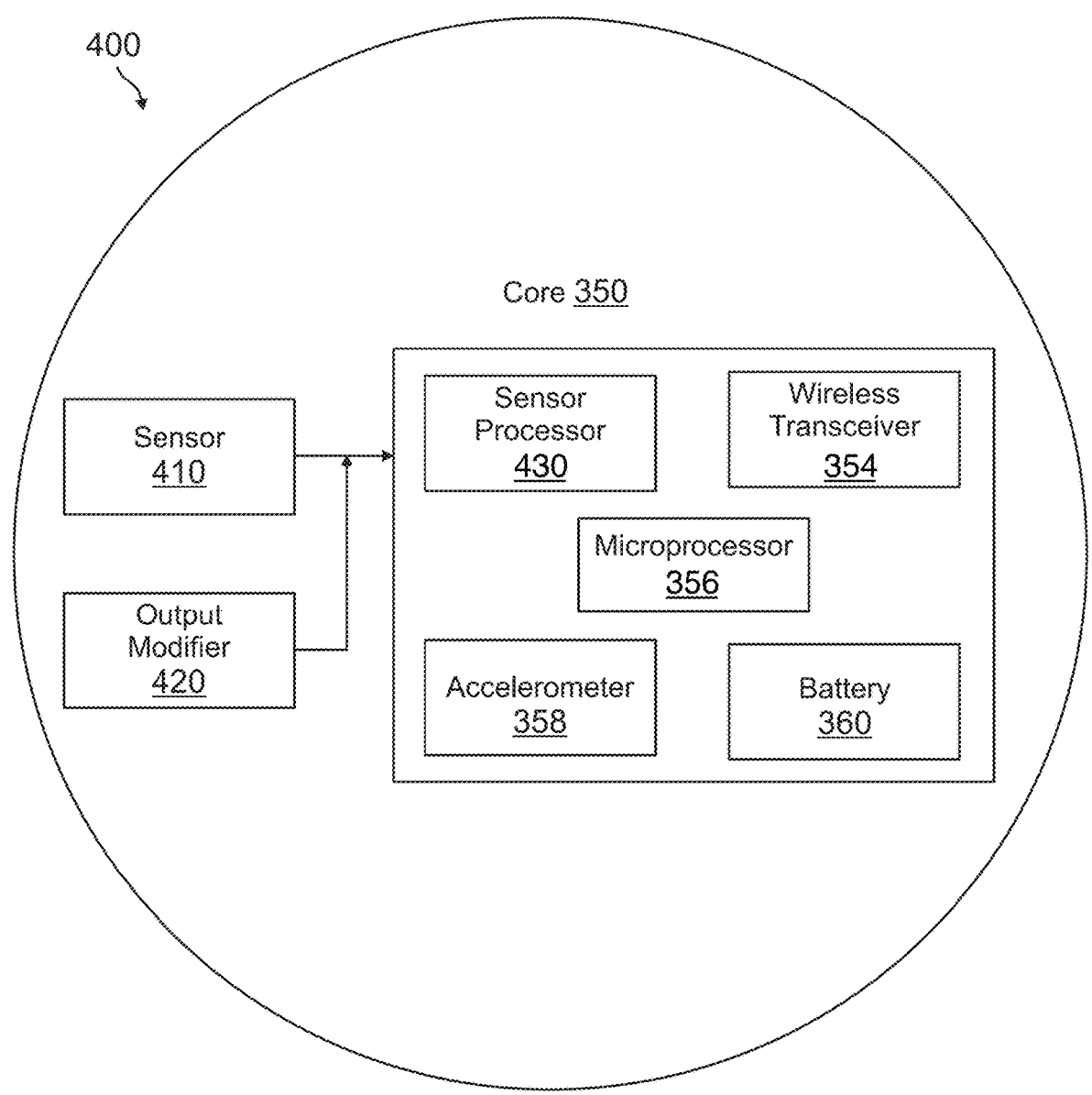
FIG. 4 is a diagram conceptually illustrating one embodiment of a sensorized sphere's inner core hardware components.

FIG. 4 further depicts the hardware and electrical components, and connections of a sensorized sphere according to one embodiment. As shown, sensorized sphere 400 has sensors 410 and output modifier circuit 420. Output modifier circuit 420, although not shown here, is electrically connected to binary modifiers 120. The core includes a microprocessor 356 which includes, or in one embodiment, is electrically coupled to a sensor processor 430 which processes the signals of the sensor 410 and output modifier circuit 420. In one embodiment, the microprocessor 356 is electrically coupled to an accelerometer 358 and wireless transceiver 354. In one embodiment, the microprocessor 356 receives signals from the sensor processor 430 and accelerometer 358, and relays the signals to a wireless transceiver 354, which provides the signal output to a remote radio frequency (RF) receiver. The microprocessor 356 may also process feedback from battery 360 to alert the user of a low battery charge or to indicate the status of the battery. The output modifier circuit 420 as discussed earlier (in reference to binary modifiers 120) may modify the signals of sensor 410. In one embodiment, the binary modifier circuit 420 communicates directly with microprocessor 356 to transmit signals related to binary modifiers 120. For example, when binary modifiers 120 are triggered by the user, the output modifier circuit 420 may process such binary functions and change the corresponding signals of sensors 410 as processed by sensor processor 430. The signals are further received and processed by microprocessor 356 as shown here and eventually relayed through wireless transceiver 354 to a user interface or audio output such as speakers, a user's computer, smartphone, or on the sensorized sphere itself. The accelerometer 358 may record the acceleration and movement of the sensorized sphere and such data may be processed by microprocessor 356 for relay to transceiver 354. Wireless transceiver 354 may also receive signals from a user remote computer as shown in FIG. 6 to program the microprocessor 356 or sensor processor 430, which may include user firmware or software installed on microchip memory.

Figure 5:
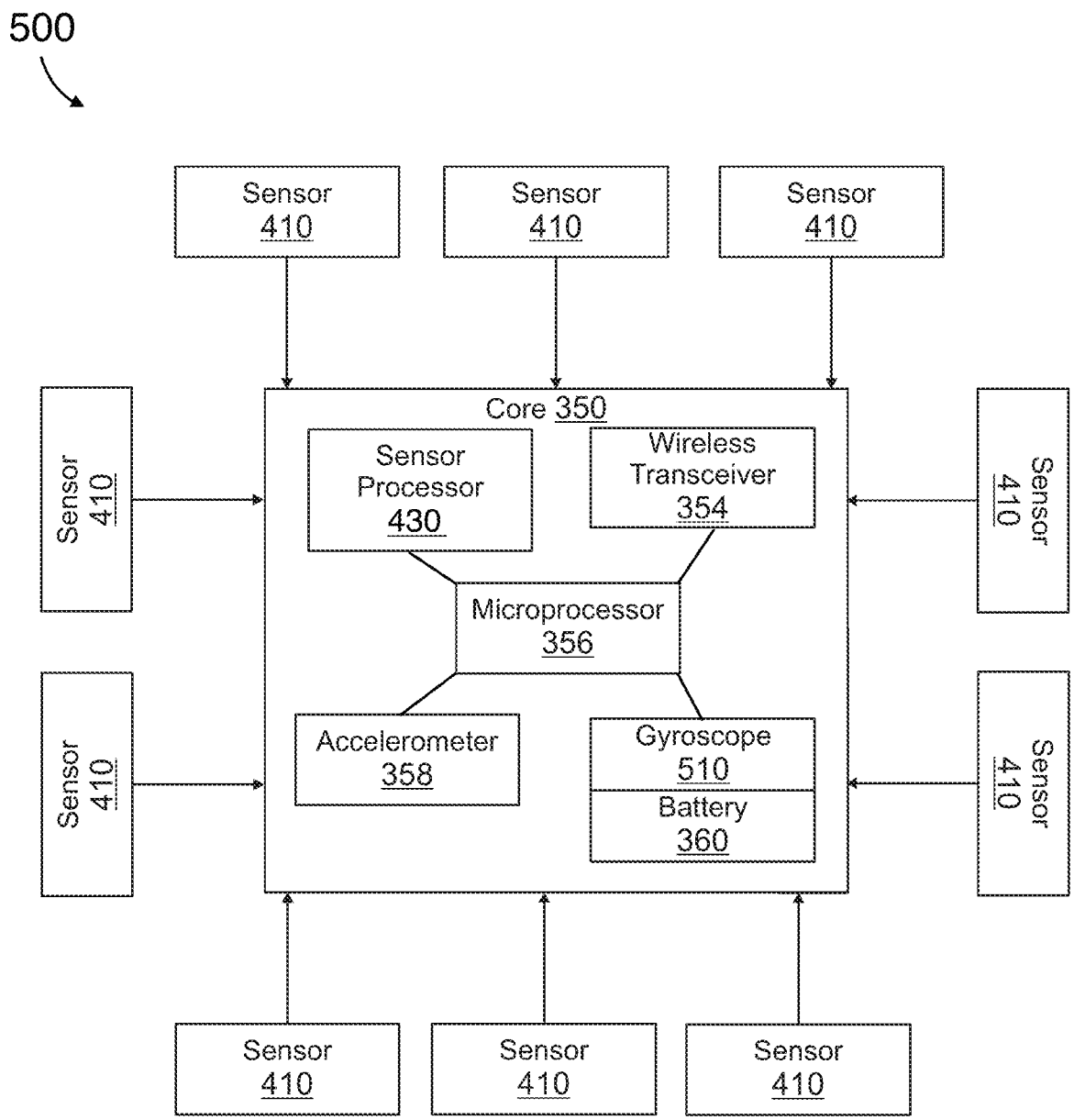
FIG. 5 is a hardware architectural diagram of the sensor connections to the inner core electrical components of the sensorized sphere, according to one embodiment.

FIG. 5 depicts another embodiment of the electrical components 500 of a sensorized sphere with ten sensors including additional components such as gyroscope 510. In this embodiment, each of the sensors 410 is shown in communication with the core 350, which includes sensor processor 430, microprocessor 356, wireless transceiver 354, accelerometer 358 and gyroscope 510. In one embodiment, the gyroscope 510 may sense angular momentum and velocity. When the gyroscope is rotated as a result of the user's actions and handling of the sensorized sphere, the gyroscope sensor may drive vertical vibration or rotate the sphere. As discussed herein, the various sensors 410 are in constant feedback and communication with the sensor processor or microprocessor to provide data feedback on the user's actions which are transmitted through the wireless transceiver to a remote application, smartphone, tablet, laptop or desktop computer. In this manner, the sensorized sphere collects and captures data across several parameters, which can be measured by various sensors (e.g. touch, pressure, force, electrical capacitance) as well as through accelerometer 358 and gyroscope 510. The combination of movement, user gestures, and user input through activation of the sensors 410 may result in various and diverse signals and inputs which are processed by the sensor processor and core microprocessor for eventual feedback and data output to a user computing device.

FIG. 6 depicts one embodiment of a user computer 600 electrically coupled to the core 350 of a sensorized sphere 100. Computer 600 depicts a functional block diagram illustration of a typical computing platform. Computer 600 may consist of a general purpose computer, a special purpose computer, a tablet, smartphone, or any other suitable computing device known to one of ordinary skill in the art. The computer 600 includes a processor or CPU 610, in the form of one or more processors, for executing program instructions. The exemplary computer platform includes an internal communication bus 660, program storage and data storage of different forms, including storage device 690, read only memory (ROM) 680, or memory 670 (e.g. RAM or flash memory), for various data files to be processed and/or communicated by the computer, as well as possible program instructions to be executed by the processor CPU 610. The computer 600 also includes I/O components such as keyboard 692 and mouse 694, supporting input/output flows between the computer and other components therein such as the touch screen of a computer tablet device or smartphone.

The computer 600 may also receive programming and data via network communications through the receiver 620 and communicator interface 630 which may include any number of inputs such as USB, or any number of various wired or wireless protocol inputs known to one of ordinary skill in the art. The computer 600 also includes a display 650 and graphical user interface 640 for output of data signals from the sensorized sphere to the user's computer 600. The GUI 640 itself may be a touch screen display which serves as an input and output device for communications with the core 350 of the sensorized sphere. The graphical user interfaces are described in further detail in FIGS. 11-14.

In one embodiment, computer 600 may be used to program audio or data files associated with each of the sensors 410. For example, if the sensorized sphere is to serve as a musical instrument, in one embodiment, a user may program audio files or musical notes through computer 600 which are stored in the storage device 690. The data or audio files will be subsequently activated by a user through sensors 410 and the output of such signals will be communicated through the receiver 620 or communicator interface 630 and processed by the processor 610 or firmware or software resident on the user's computer or computing device 600. The output may then be displayed to the user via the GUI 640 or output through some other means such as a sound card on the user's computer to the user's speakers.

Figure 7:
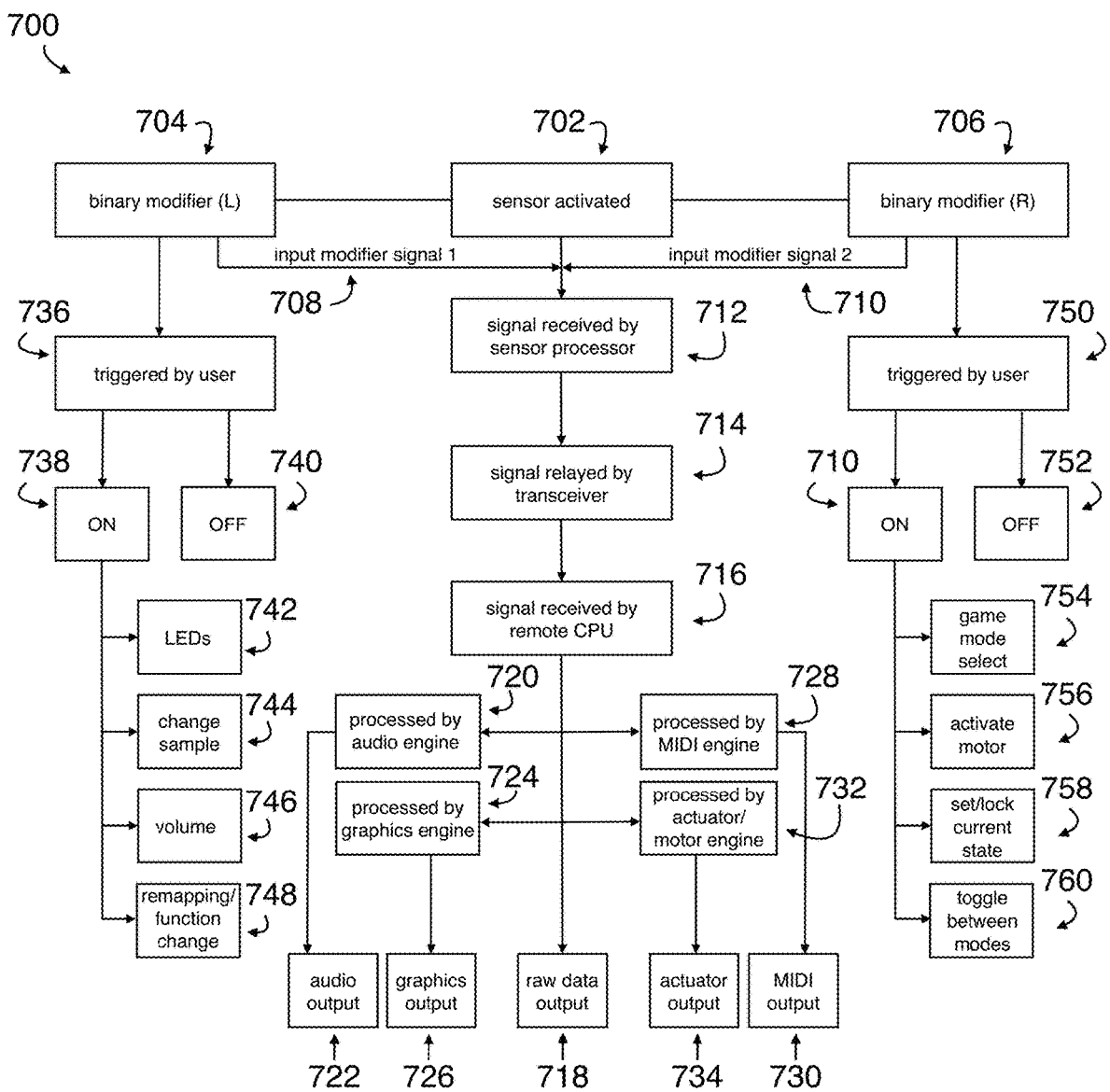
FIG. 7 is a flow diagram illustrating the signal processing of sensorized sphere with resulting output according to one embodiment.

FIG. 7 shows a computerized flow diagram 700 depicting the signal processing of a sensorized sphere according to one embodiment. In this embodiment, one or more sensors are activated by user gestures at step 702. The user also has the option to activate the left binary modifier 704 or the right binary modifier 706. If the user activates the right binary modifier, then input modifier signal 1 (708) is transmitted to the sensor processor. If the user activates binary modifier 706, input signal modifier signal 2 (710) is transmitted to the sensor processor. If the user does not activate one or more of the binary modifiers, the sensor signal, e.g., from the force sensors, is transmitted to and received by the sensor processor at step 712. The sensor signal or signals are then relayed by the RF transceiver at step 714 and then sent to a user computer, where the signal is received by the remote CPU at 716. The sensor signal is then processed by software modules on the user computer and results in raw data output in step 718. That output may be translated to audio, graphics, raw data, actuator output, MIDI, OSC, or other multimedia outputs. In one embodiment, the sensor signal is processed by the audio engine in step 720, resulting in audio output 722. As discussed herein, the audio output can be any unique audio file corresponding to the activated sensor. In another embodiment, the sensor signal or data is processed by a graphics engine in step 724, resulting in graphics output 726. As discussed herein, the graphics output can be any unique graphics or visual data file corresponding to the activated sensor signal. In another embodiment, the sensor signal or data is processed by a MIDI engine at step 728, resulting in MIDI output at step 730. In other embodiments, the sensor signal can be processed by actuator or motor engine at step 732, resulting in actuator output at step 734.

The left and right binary modifiers 704 and 706 can also trigger different functions for the sensorized sphere in some embodiments. For example, if the L binary modifier 704 is triggered by user at step 736, it can either be set to an "on" position 738 or "off" position 740. In the "on" scenario the binary modifier 704 can effect a number of different functions, including activation of LEDs 742, change of audio/visual sample 744, adjust volume 746, or remap and change function at 748, which may include changing audio samples or data file associated with particular sensors. Similarly, the right binary modifier 706, if triggered by the user at step 750, can be set to an "on" position 710 or "off" position 752. If in the "on" position, the binary modifier can effect functions such as game mode selection 754, activate motors at 756, set or lock current state 758 of sensor output or toggle between different modes 760. In these embodiments, the right and left binary modifiers, are able to trigger a number of different functions for the user from changing the audio sample, visual effects, volume, sound effects and other variety of functions. The functions provided here in 742-748 and 754-760 are exemplary and one of ordinary skill in the art can program any number of customized user functions that are triggered by the binary modifiers.

In one embodiment the sensors are activated at step 702 through force, linear potential or some other capacitive means. The binary modifiers may also serve to affect modifications of signal output such as sample playback speed (or filter sweeps, panning, amplitude) through signal modifiers 708 and 710; before being further processed by the audio engine 720. For example, if the binary modifiers 704 or 706 are activated, the resulting input modifier signals at step 708 or 710 can uniquely change the sound, speed, frequency, octave, or other musical or visual functions that are processed by the audio and graphics engines.

Also, in one embodiment, the binary modifiers 704 or 706 may activate a gate to affect the filtering of the audio output signal. In this embodiment, the sample playback speed and filter sweep can also be depicted at GUI 640 at the user's computer 600. The audio filtering may also be activated or adjusted from input from the accelerometer 358, such that higher acceleration of the sphere by the user may increase or decrease the frequency of the filter sweep. The combination of the sensor inputs, binary modifier inputs, and IMU may result in an elaborate change in the tone, pitch, volume or frequency of the audio file that is linked to each sensor input. In this way, the sensorized sphere serves as a complex musical instrument and control structure enabling the user to simultaneously play music and adjust frequency and tempo of programmed beats, musical notes and tunings, samples, and other features, by movements of the ball.

Figure 8:
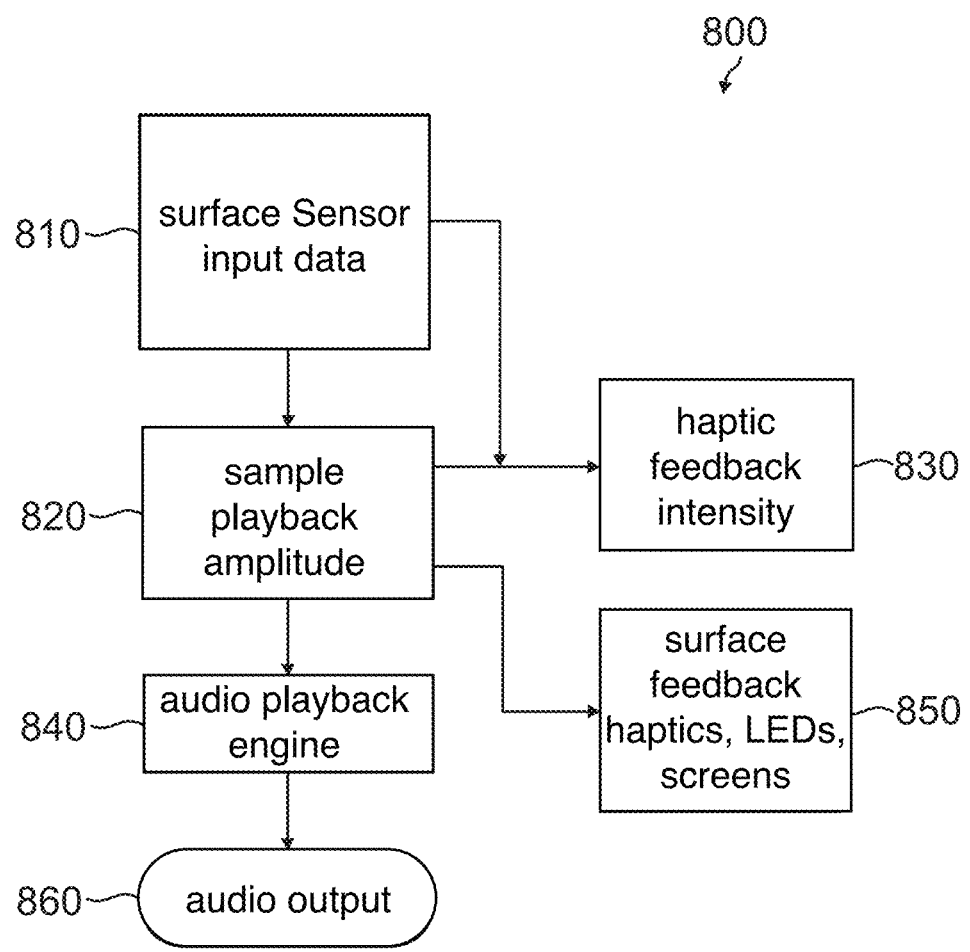
FIG. 8 depicts an embodiment of the signal processing flow diagram of a sensorized sphere with resulting output to a remote computer and to the sphere itself.

FIG. 8 depicts an architectural flow diagram 800 of signal processing from an embodiment where the surface sensors are linked to surface feedback elements such as haptic feedback motors, LED lights and screens. For example, in this embodiment an activated sensor at step 810 may trigger a sample playback 820, the amplitude or intensity of which may be affected by the duration, force, or capacitive input of sensors 110. If the amplitude of the signal reaches a certain threshold, this may trigger haptic feedback to the user in the form of haptic feedback intensity 830 on a scale of 0.0 to 1.0, with 1.0 being greater haptic intensity. The sample playback 820, when activated, may also involve surface feedback 850 in the form of LED lights or one or more display screen(s), or other visual media displayed on the surface of the sensorized sphere. The audio playback signal proceeds to the audio playback engine 840 before transmission to audio output 860 which may include speakers on the sensorized sphere or audio output on the user computing device 600; or on some other audio output device enabled to receive data and/or audio signal from the sensorized sphere.

Figure 9:
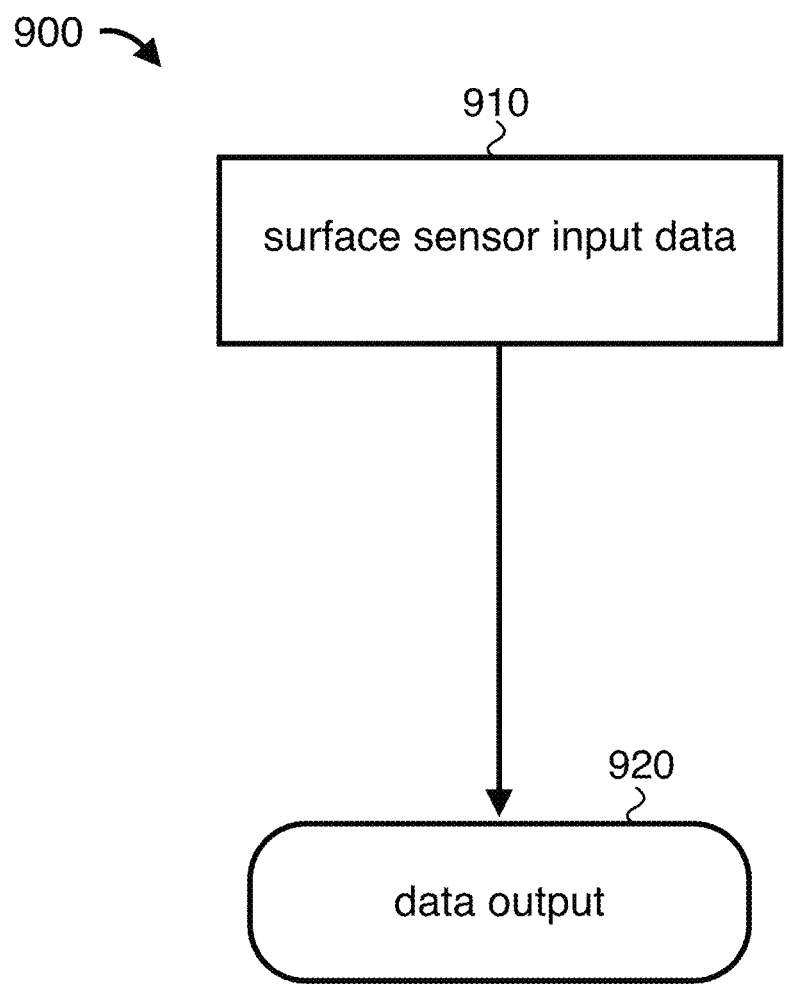
FIG. 9 depicts an embodiment of the signal processing flow diagram of a sensorized sphere with resulting data output.

FIG. 9 depicts an embodiment of a sensorized sphere data output signal flow 900. Not all embodiments involve musical or audio outputs. In this embodiment, the sensor pad 110, when activated, results in a data output to a user computing device 600 or on the surface of the sensorized sphere itself. For example, a data output from the surface sensor may include a graph or timeline of the user's movements with the sensorized sphere 100, including a measurement of the user's force enacted upon the sensor pads 110, the total movement, acceleration, and speed of the ball; as well as the total amount of time that the user has played with the sensorized sphere, and whether or not they have completed certain milestones.

Figure 10:
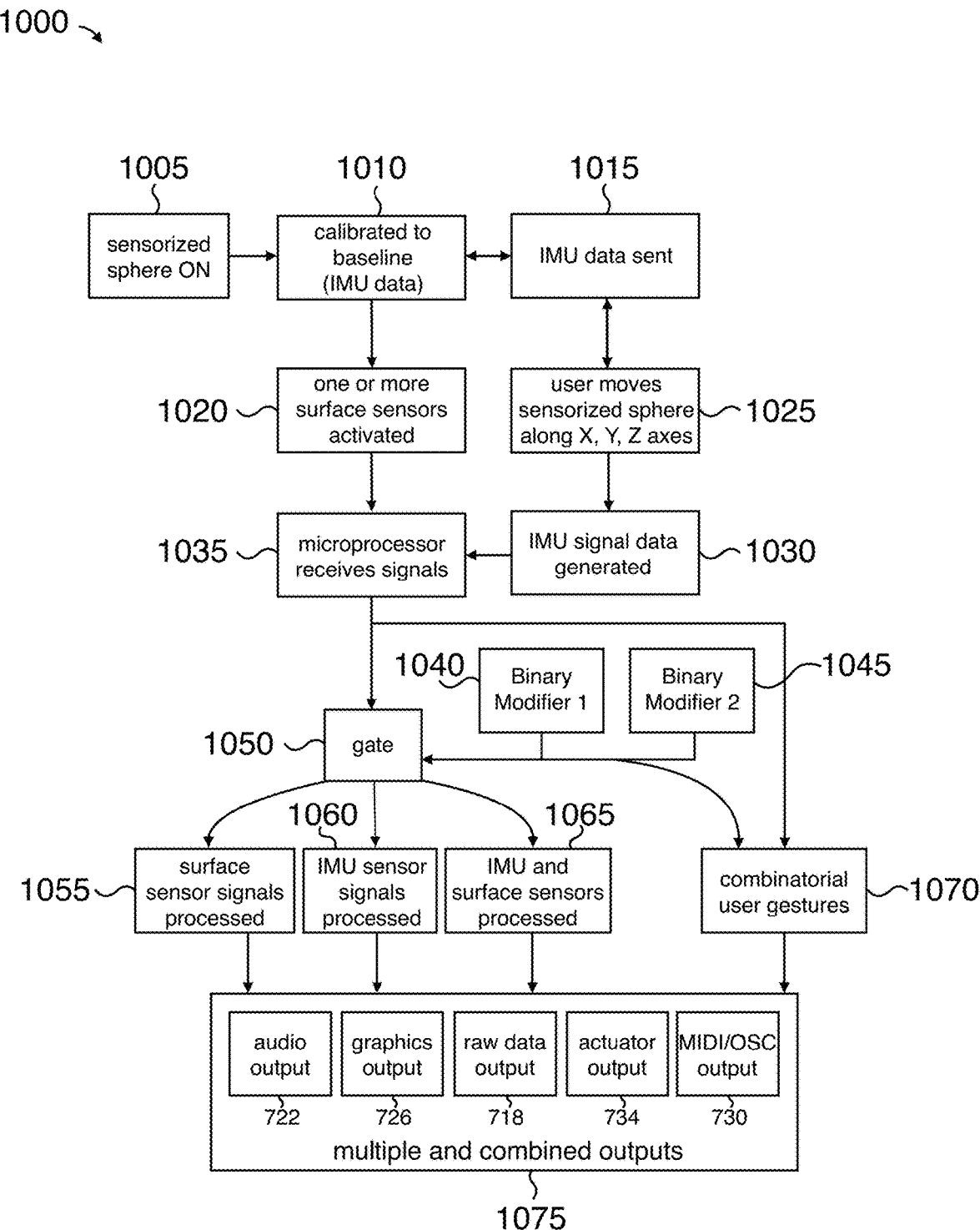
FIG. 10 depicts an embodiment of the signal processing flow diagram of a sensorized sphere with IMU sensors and binary modifiers.

FIG. 10 depicts the electronic and computerized signal processing of one embodiment 1000 that includes activation of surface sensors, inertial measurement unit (IMU) sensors, and binary modifier functions. IMUs may include accelerometers, gyroscopes, magnetometers, or any combination of these sensors or any other inertial measurement processing sensor known to one of ordinary skill in the art. IMU input can be measured along the X, Y and Z axis as the sphere moves through space in different directions. Such data may also include velocity data, acceleration data, spin data, distance data, directional data, and any other data that is capable of being measured by IMU sensors. In one method embodiment, the sensorized sphere is in the "on" state 1005. The sphere and software is calibrated to a baseline state e.g., "0" or some threshold value based on the data from the IMU and/or force sensors. For example, the IMU can calibrate the sphere and its software, based on values emerging from the X, Y and Z axis inputs; and that data can be calibrated to a steady state (for example, when the ball is in a cradle or some other device such as a charging station). The user may also calibrate the sensorized sphere to be in an "on" and "ready" state while the sphere is being held in their hands; but simultaneously in such a way, that the values emerging from the sensors may not have yet reached their sufficient (predetermined, calibrated) threshold value, necessary to generate signals that would result in audio or visual outputs. In step 1015, IMU data is sent to the microprocessor to signal a calibrated baseline state. In step 1020, one or more surface sensors are activated. This may happen, for example, when the user grasps the ball and applies enough force to activate one or more surface sensors which are spaced relative to the fingers of an average human hand. As described herein, the surface sensors may be on top of the sphere or embedded under a top layer or various layers of the sphere. The sensor may also be embedded between different layers such as a resistive and capacitive layer to allow for a threshold value of force to activate the sphere, so that such sensors are not overly sensitive to user gestures and grasps, but rather require some additional threshold force or IMU values for activation. Step 1025 depicts the signal flow when IMU data changes from the baseline state upon the user's movement of the ball along either an X, Y, or Z axis in space, or some combination of movement across three-dimensional space. IMU signals are generated in step 1030 and sent to the microprocessor in step 1035. The microprocessor may receive signals from either or both the surface and IMU sensors. In one embodiment, binary modifier 1040 is activated, sending a signal to gate 1050. Binary modifier 2 can be activated in step 1045 which can independently or in combination send data to the gate 1050 with Binary Modifier 1 in step 1040. In one embodiment, the signal from the force or surface sensors independently proceeds to step 1055 before it results in output 1075. In another embodiment, the IMU sensor signals are independently processed at step 1060, resulting in output 1075. In another embodiment, IMU and surface sensor data is combined and results in output 1075. In yet another embodiment, the input from binary modifiers 1 or 2, or both, is processed at gate 1050, or further added to the signals from surface sensors or IMU data, resulting in output 1075. A user's unique gestures while interacting with the sensorized sphere (using surface sensors, IMU data, and binary modifier functions), can result in combinatorial user gestures 1070, which results in an unique output 1075. This can be used, for example, to unlock keys, change or adjust functions for different use cases, navigate game modes, or create a number of unique gestural outputs illustrated in block 1075. Output 1075 may include any number of different outputs on a computerized device, on the sensorized sphere itself, on panel displays, speakers, wireless motors and to other devices capable of receiving RF feedback. Embodiments include audio output 722, graphics output 726, raw data output 718, actuator output 734 and MIDI or OSC output. Each of these outputs may occur independently or in combination, depending on the unique gestural handling of the sensorized sphere by the user, and the signals generated by the surface sensors, IMU sensors or binary modifiers. It is contemplated that a user can create potentially millions of different outputs and combinations depending on the combination of surface sensor activation (and continuous data values), IMU data, and binary modifier functions. For example, a user's depression of 10 different force sensors in a variety of permutations with added IMU signal modification coming from the sphere moving in 3d space can unlock millions of unique combinations which can be processed and generated in millions of unique outputs across a variety of audio and multimedia devices, graphics displays, and other raw data outputs which can be translated into sight, sound, and movement. There are potentially infinite permutations of combined user gestures and translated outputs. In a musical and therapeutic setting, this can have enormous benefits in training and developing motor skills, and sight and sound combinations can activate unique outputs for the user to monitor their progress. In one embodiment, the sensorized sphere can be combined with MM (magnetic resonance imaging) data to reveal real time brain imaging that translates user's gestures (while interacting with the sensorized sphere) into visual maps of the user's brain, showing activation and neuronal activity in specialized regions of the user's brain. Other brain mapping software and devices known to those with ordinary skill in the art can be used with the sensorized sphere in medical or therapeutic settings.

Depending the on the movement of the sensorized sphere along an X, Y, or Z axis, when a certain threshold is reached (for example along a scale of 0.0-1.0, with 1.0 representing more movement along an X, Y or Z axis, or movement towards one or more axes), IMU data 1030 may be generated to affect the sample playback functions of audio outputs. In one example, according to the user's quick or gradual movement of the sensorized sphere through space and accompanying activation of the accelerometer, the sample playback speed may be accelerated or decelerated in audio output 722. For example, faster acceleration of the ball through space may increase the speed of audio output. In another use case, the acceleration or movement of the sphere may affect the filter sweep of the signal resulting in an increased frequency of the sound signal in audio output 722. Signal frequency and musical tunings and pitches may also be increased or decreased depending on IMU data.

In one embodiment of the invention the sensorized sphere can be calibrated or programmed through machine learning. Machine learning refers to a group of statistical analysis methods that learn from training by example, allowing for inference and generalizations of complex data structures, and pattern identification and comparisons with pre-existing or previously trained patterns. B. Caramiaux and A. Tanaka, "Machine learning of musical gestures," in Proc. International Conference on New Interfaces for Musical Expression, 2013. This process is divided into two phases of training (learning from a series of data samples) and testing (taking new samples and inferring decisions based on its previously-learned data structure). Different training approaches are applied according to each scenario. Some common strategies are: supervised, unsupervised, and semi-supervised. A supervised learning algorithm can be used when the output goal is known, training with data pairs of corresponding inputs and desired outputs. This may be musically meaningful when mappings specific gestures to discreet musical output scenarios. An unsupervised learning approach may be useful when the goal is unknown and will be learned from the data. This may be helpful when attempting to understand data patterns representing discursive and complex sets of user input data, and in grouping these data into categories. Semi-supervised approaches combine a supervised approach (considering pairs of outputs with their desired outputs) with a refining of the data by considering more unanticipated data.

In one type of supervised learning algorithm, any type of N-dimensional signal may be classified by fitting M clusters to each data class during a (machine learning) training phase. A new data sample can then be classified by identifying the cluster with minimum divergence from the new sample. This is useful for mapping musically-meaningful gestures that will naturally vary slightly as the user moves the sphere in three-dimensional space, over time.

The following table depicts an exemplary relationship between data sets from a user's interaction and training input with a sensorized sphere to corresponding machine learning signals and mapped output functions:

Therefore, according to embodiments described herein, complex (but reproducible) physical gestures with a sensorized sphere can be trained and identified for mapping to specific musical outputs. These relationships may be defined by preset parameters, but can also be defined by allowing a user to train new and unique customized gestures to their preferred musical or data outputs. This is especially helpful in a therapeutic setting when calibrating the sphere's system to accurately reflect the movements and spherical interactions of a patient with physical and/or cognitive impairments. Such users' ability to express certain gestures with their body, will often improve throughout their therapy. In one embodiment, machine learning algorithms would allow the mappings to evolve comfortably with a patient's individual rehabilitation progress with the sensorized sphere.

One embodiment makes use of time series analysis (a series of temporally-indexed data points), dynamic time warping is an algorithm that may be employed to measure similarity between two temporal data sequences, which may be varying in speed over time. Dynamic time warping can be used to find pattern-similarity even as internal temporal relationships may be inconsistent between samples. This is

TABLE 1

| Training Input | IMU Data (accelerometer, gyroscope, magnetometer) (M Clusters) | | | | | | Force Sensors | Machine Learning Function (N Signal) | |
| --- | --- | --- | --- | --- | --- | --- | --- | --- | --- |
| | X axis - value (X) | Y axis - value (Y) | Z axis - value (Z) | Acceleration (a) | Velocity (v) | orbital velocity (ov) | Force value (F) | f (x, y, z, a, v, ov, F) = N | Output |
| Gesture 1 | X1 | Y1 | Z1 | A1 | V1 | Ov1 | F1 | 10 | Rhythm1 |
| Gesture 2 | X2 | Y2 | Z2 | A2 | V2 | Ov2 | F2 | 9.5 | Rhythm1 |
| Gesture 3 | X3 | Y3 | Z3 | A3 | V3 | Ov3 | F3 | 10.5 | Rhythm1 |
| Gesture 4 | X4 | Y4 | Z4 | A4 | V4 | Ov4 | F4 | 15 | Rhythm2 |
| Gesture 5 | X5 | Y5 | Z5 | A5 | V5 | Ov5 | F5 | 14.5 | Rhythm2 |
| Gesture 6 | X6 | Y6 | Z6 | A6 | V6 | Ov6 | F6 | 15.5 | Rhythm2 |

In one embodiment, the user's interactions with the sphere in three dimensional space are measured by IMU data across x, y, and z axes, acceleration data (a), velocity data (v), orbital velocity data (ov) and force values (F) resulting from the user's movement and gripping of the sphere. The method may also capture angular velocity, rotation and other data points and their combinatorial sets. For example, the user may be gripping the ball, activating a combination of force sensors, and also rotating the ball through 3D-space to create a unique gesture. These movements will be translated to data via the IMU sensors and the force sensors. Data from these sensors can be defined as M-clusters. A machine learning function or algorithm can be defined to generate an N-signal value which in one embodiment is a machine learning mathematical function (f) of (x, y, z, a v, ov and F). The M-clusters may consist of data points from any number of the IMU or F sensor input data values. For example, in one embodiment, as shown in Table 1, Gestures 1, 2 and 3, generate N-Signal values of 10, 9.5 and 10.5. In this example, the machine learning algorithm for the sensorized sphere correlates values within 0.5 of mean value 10 as corresponding to Rhythm1. In this embodiment, a user may also interact with the sensorized sphere to generate Gestures 4, 5, and 6. These gestures generate N-Signal values of 15, 14.5, and 15.5, through a machine learning mathematical function (f) of (x, y, z, a, v, ov, and F). These values which have standard deviation of 0.5 from the mean value of 15 can be used to map to a unique output of Rhythm2.

useful in developing musical mappings that recognize certain user gestures regardless of varying speeds over time.

The technique of regression uses supervised learning and is the task of modeling samples of an unknown function by learning to identify the function generating the samples, and based on samples of input variables paired with their target variables. The relationship between input and output is a function learned by the method. This may be used for gesture representation and to map simple, linear relationships such as between acceleration and audio amplitude, as well as more complex combinations of non-linear data combinations. For example, the sphere's movements in three-dimensional space may be represented as a concatenation and integration of a variety of gesture parameters observed over time. Data parameters such as upward, downward, and lateral force; X, Y, Z movements and acceleration; and 3-dimensional angular velocity can all be combined to represent and musically map, dynamic and complex user gestures, and unlock complex sets of musical (and multimedia/multimodal) outputs.

The technique of classification is the task of categorizing datasets into groups called classes and deciding to which categories these datasets pertain. Unlike the continuous output of regression, classification provides a discreet, high-level representation of user gesture. In classification, continuous input variables are labeled as discreet gestural classes. During the testing phase, a new input sample is assigned an output label. This method can allow us to categorize certain qualities of discreet musical gestures and patterns in ways that continuous streaming input cannot.

A common method of classification useful for musical interfaces and sensorized devices that employ simultaneous multidimensional data streams (such as the sensorized sphere), are Artificial Neural Networks. These methods can be useful in cases where there may be non-linear noise and data redundancy across a dynamic set of multidimensional inputs, and in mapping these reliably and meaningfully to reproducible musical (and multimedia) outputs as described herein.

Figure 11:
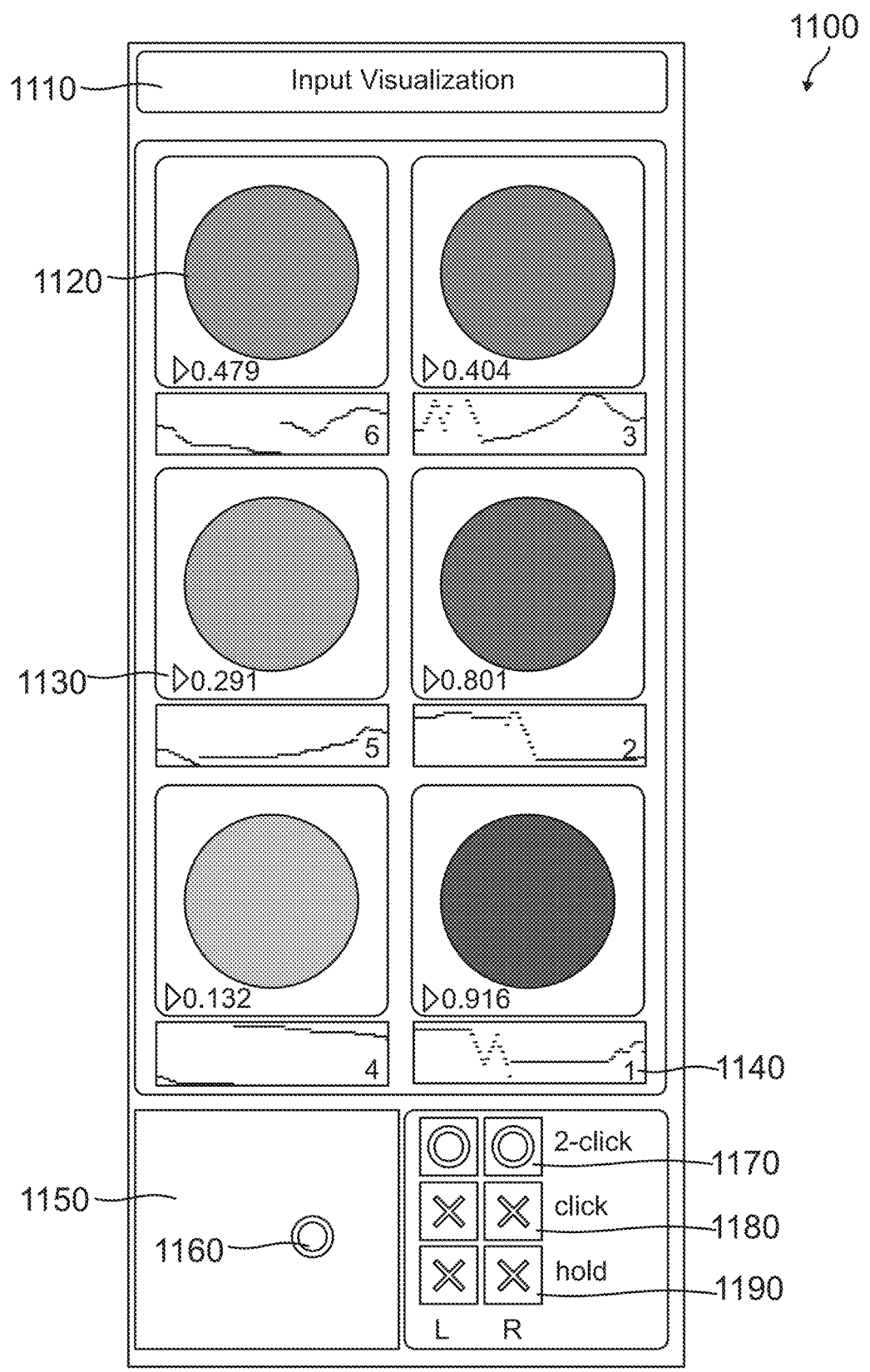
FIG. 11 depicts an embodiment of the output of individual sensors to a user interface for software that is connected to a sensorized sphere.

FIG. 11 depicts a graphical user interface 1100 corresponding to individual sensors of the sensorized sphere 100 according to one embodiment. In one embodiment, a GUI prototype is developed using Max/MSP/Jitter, an object-oriented graphical programming language that integrates data flow (Max), signal processing (MSP), and matrix processing (Jitter). Max is maintained and developed by Cycling '74. (cycling74.com). Input visualization 1110 shows a color or tone graded visualization of each of the separate sensors 110 on the left and right side of the sensorized sphere 100. The circle 1120, of which there are six depicted in this example, show various different shades of color tones, corresponding to the force applied on each sensor 110, with floating point values also shown in the corresponding decimal numbers 1130, with "1" representing the highest force that can be applied and measured by each sensor. As shown, the higher number values in 1130 correspond to darker shades of color for the represented sensor circles 1120. Mini-graphs 1140 depict the force or pressure applied over time to each of the sensors, according to one embodiment of the invention. Area 1150 in the GUI shows the location of the sensorized sphere in two-dimensional coordinates. For example, in this embodiment, if the sensorized sphere is moved to the right the circle 1160 will move in the screen along the X-axis. If the ball is moved up or away from the user, the circle 1160 will move up along the Y-axis in the screen area 1150. Icons 1170, 1180 and 1190 provide a visual depiction of the state of the sensor modifiers 120. In this embodiment, if the binary modifier is clicked twice on either the left (L) or right (R) side, the 2-click icon will be activated. If it is clicked once, then click icon 1180 will be activated. If it is held down or pressed for a length of time, icon 1190 on L or R side will be activated. As discussed herein, binary modifier 120 through single click, double click or hold functions will change the sensor signal, by modifying its output. In this way, an audio file's speed, frequency, amplitude or other parameters may be adjusted. Different sounds, notes, or tracks may be changed depending on the state of the click or hold functions. Also, in other embodiments, the click, double click, or hold functions may change the data output by modifying a cursor, color or graphic on the user's GUI, thereby allowing the user to use the sensorized sphere as an interactive graphical output with sensor and modifier buttons allowing the user to playback and live process visual media. The medical and rehabilitative uses of such an interactive sensorized sphere with user-modifiable outputs have vast potential implications for studying and practicing new rehabilitative and therapeutic approaches. A patient who has limited or impaired motor functions can gradually track their improvement by the changing the scope and elaboration of visual outputs being rendered on-screen by the user's own interactions with the ball. Increased use and performance, measurement of individual finger digits, and the ability to move the sensorized sphere in different directions can all be measured and collected by a doctor, therapist, or clinician monitoring patient progress.

Figure 12:
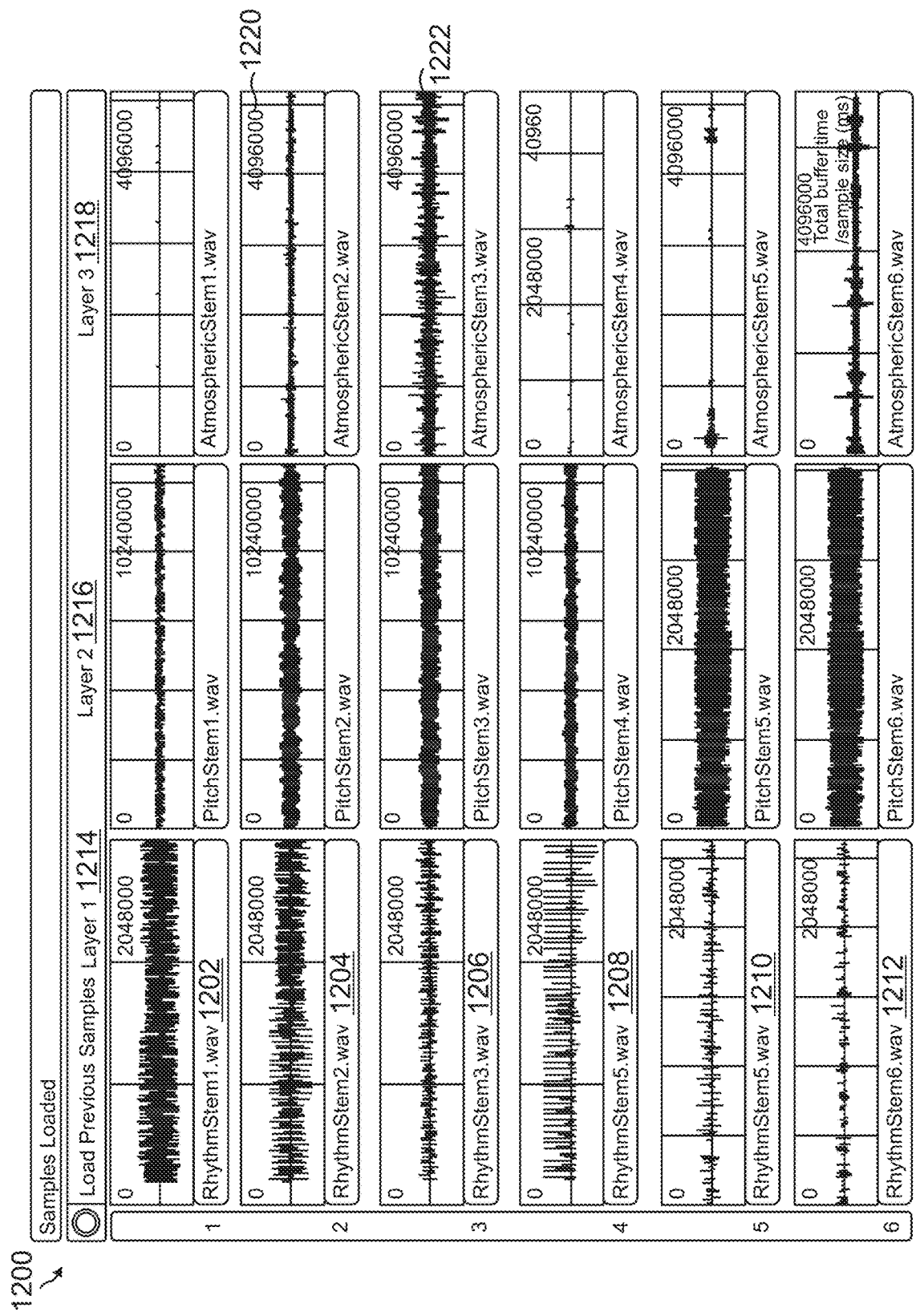
FIG. 12 depicts an embodiment of the graphical waveform output of individual audio/data files that correspond to sensor outputs from a sensorized sphere.

FIG. 12 represents a graphical user interface 1200 of audio samples corresponding to three different layers for each sensor input 110. The column bar on the left of 1200 represents each sensor 1-6 in this embodiment. Sample layer 1214 represents one type of audio file. In this example, RhythmStem1.wav through RhythmStem6.wav are loaded for each of the six sensor inputs. These are all rhythmic, groove-oriented samples. Layer 1216 includes a second set of audio files. In this example, PitchStem1.wav through PitchStem6.wav are loaded for each of the audio inputs corresponding to sensors inputs 1-6. These are all pitched sounds (musical tones) and can be used to compose, improvise, and perform melodies and harmonies. Layer 1218 includes a third set of audio files. In this example, AtmosphericStem1.wav through AtmosphericStem6.wav are loaded into layer 3 for sensors 1-6. These are all atmospheric and ambient sounds. As discussed herein, each Layer 1214-1216 may be activated by binary modifier 120 input by the user. In this example, the user can control 18 different audio outputs with the six sensor inputs 110. Different combinations of audio files may be played back by the user using Layers 1214-1216. GUI 1200 also depicts the waveform 1222 for each of the audio files, showing the frequency and amplitude of each of the sensor inputs 110. Time data is shown in 1220, as millisecond values for each of the audio files depicted in this embodiment. The total buffer time and sample size can be visually depicted for each of the sensor inputs using this embodiment.

Figure 13:
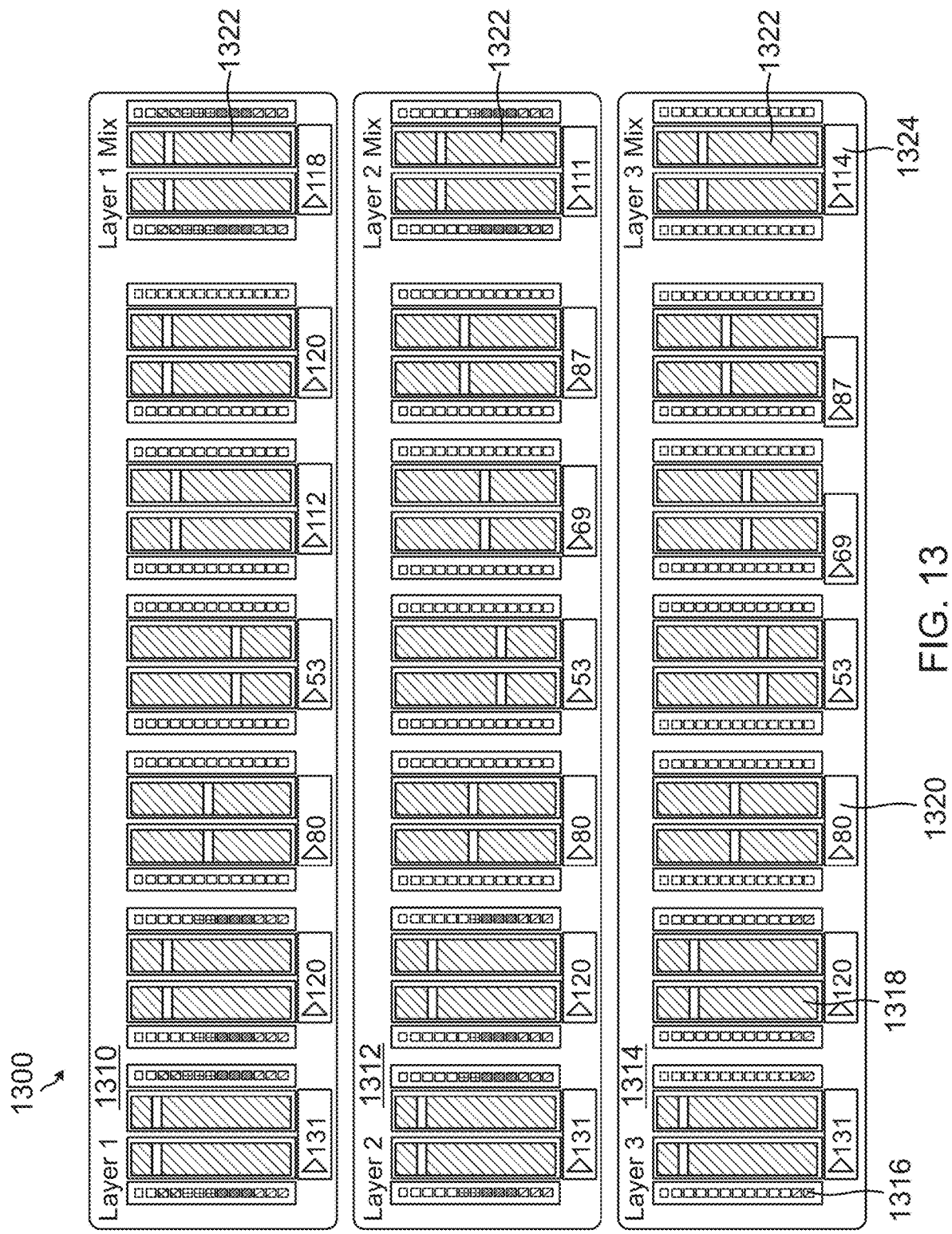
FIG. 13 depicts an embodiment of the graphical user interface control panel for adjusting the audio gain controls for outputs from each of the sensors of a sensorized sphere.

FIG. 13 depicts a graphical user interface (GUI) for a control panel 1300 according to one embodiment. In this GUI example, the user can control the audio gain (or volume) for the audio output corresponding to each of the exemplary six sensors in this embodiment. Each of the individual bars 1318 in this example may represent either gain or volume. For example, Layer 1 1310 shows the different gain or volume adjustments corresponding to each of the six sensors for Layer 1 samples. Layer 2 1312 depicts the gain or volume adjustments for Layer 2 samples. Layer 3 1314 depicts the gain or volume adjustments to Layer 3 samples. Layer Mix 1322 allows the user to adjust the combined gain or volume of each of the separate layer samples corresponding to the six sensors. Bar 1316 shows a visual representation of the gain for each of the sensors. Bar 1318 shows the gain adjustments level for each of the right and left audio outputs for individual sensor outputs. Value 1320 shows the numerical value associated with the gain for each of the individual sensor outputs. Value 1324 shows the numerical value associated with the combined gain or volume adjustment for each of the sensors. Using this GUI, the user may control the intensity of the gain, volume, and audio output for the different sensor audio files, and track layers by turning on or off the gain or volume corresponding to individual data files associated with each sensor. In this way the musical artist or clinician using the software GUI can adjust and mix the audio/data outputs in a customized fashion and according to specific use cases.

In one embodiment that contemplates ten force sensors, the device is mapped to an audio synthesizer such that each of the 10 force-sensing resistors controls the pitch and amplitude for (each channel of) the synthesizer output. Different musical scales may be mapped to the sensorized sphere and one or more pitches may be mapped to each of the force-sensing 'pads'. For example, the user may choose to map a C major scale to be output by the device; such that pad 1 will generate a C at frequency 261.626 hz (known as middle C) at the amplitude controlled by the amount of pressure applied to the surface of each force-sensing resistor. Extending the C major scale across all 10 pads would follow with pad 2 generating a D (at a frequency of 293.665 hz.); pad 3, E (at 329.628 hz.); pad 4, F (349.228 hz.); pad 5, G (391.995 hz.); pad 6, A (440 hz.); pad 7, B (493.883 hz.); pad 8, C (523.251); pad 9, D (587.330 hz.); pad 10, E (659.255 hz.). Different settings allow for different scales and ranges of frequencies that can be dynamically re-mapped by the user in realtime (using the binary switch buttons to change between these settings). In this manner, the sensorized sphere enables a wide range of musical possibilities by allowing a user to change between scales, instruments, sounds effects, and other musical mappings made possible by the unique combination of force sensors, IMU data, and binary modifiers.

Figure 14:
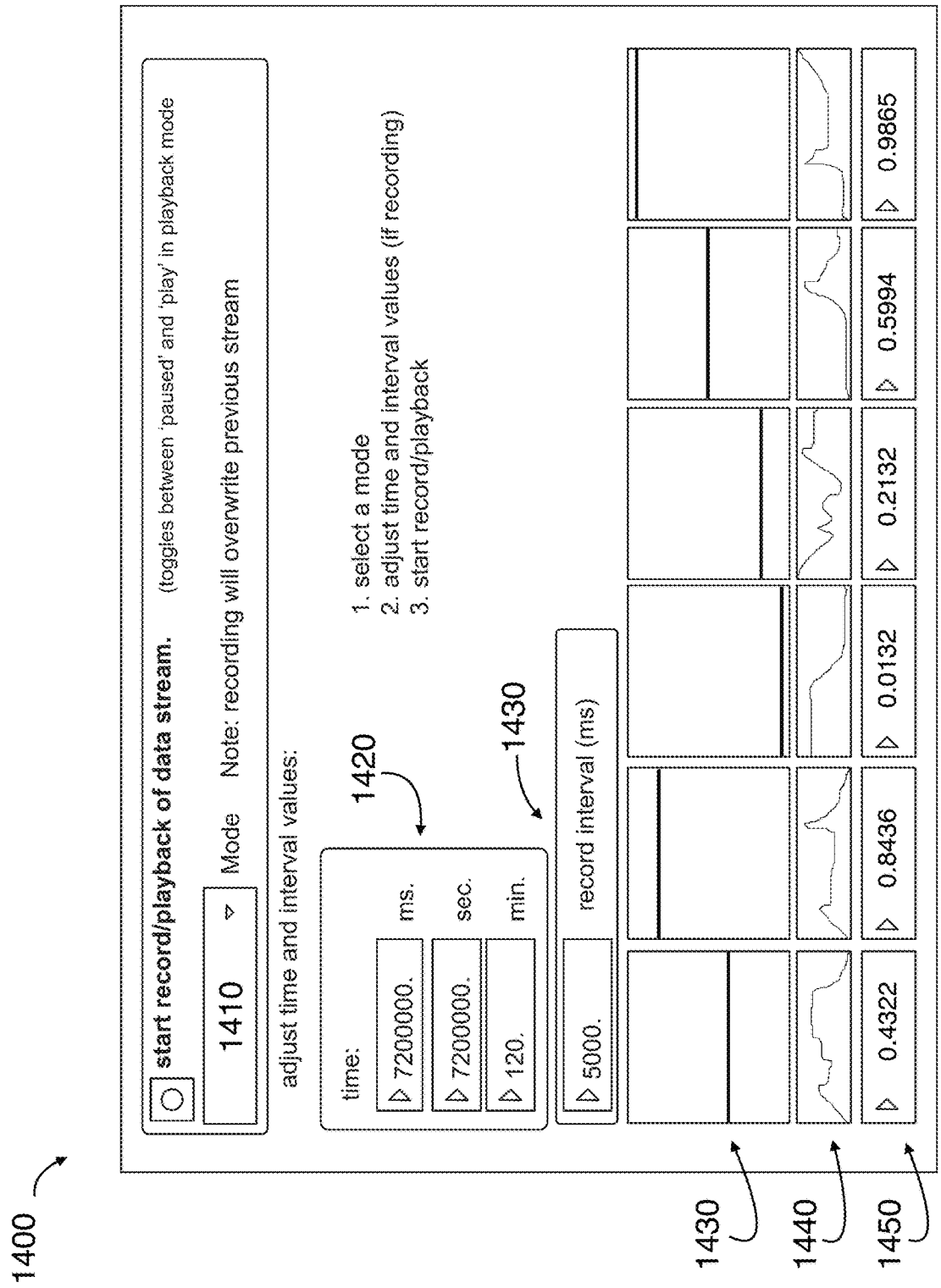
FIG. 14 depicts an embodiment of an exemplary user interface for output of signals and data from a sensorized sphere, including the recording and playing back of data corresponding to individual sensors.

FIG. 14 depicts an embodiment of an exemplary graphical user interface (GUI) for output of signals and data from a sensorized sphere, including the recording and playback of data corresponding to individual sensors. The record module 1400 includes data recording and playback features. Dropdown menu 1410 allows a user to switch between playback and record mode. Time module 1420 shows an exemplary data recording GUI which allows a user to play and record data samples labeled in minutes, seconds and milliseconds. When in "record" mode, data recorder 1430 allows the user to specify a sampling rate in milliseconds, labeled here as "record interval (ms)." 1430-1450 are interfaces that depict numerical and graphical values of individual sensors during record and playback mode. Box 1430 is a visual depiction of a bar corresponding to the numerical value in box 1450. Graphs 1440 depict the value of the force sensors over a period of time. Box 1450 shows individual numerical values corresponding to each force sensor in an exemplary six-sensor embodiment. In one embodiment, record module 1400 records and saves a list of sampled data values for each force-sensing resistor; the X, Y, and Z axes of both the accelerometer and the gyroscope (and magnetometer as desired); and time sampled, in minutes, seconds, and milliseconds. When in playback mode, the data recorder will playback a previously-recorded data stream. Having access to this data stream for analytics in a medical therapeutic environment can help patients, caregivers, doctors, and therapists, to better understand their progress (especially gradual, subtle progress) over time and across a variety of different therapeutic settings. For example a user may choose the frequency and resolution of data capture, allowing for the capture of gestures on a small time-scale, as well as the monitoring of data over days, weeks, months, or longer. A patient who has limited or impaired motor functions can gradually track their improvement (as can their therapists and doctors) by analysis of the data captured over time. The data may elucidate meaningful variations patients may bring to exercises while at home with a caregiver, versus as directed by a therapist in the hospital setting. This can help the patient care team better coordinate and adjust their methods, and can help patients better understand and perceive the therapeutic value of their efforts. It may also be able to show small but meaningful improvements in fine or gross motor skills (grip strength, or range of motion), or cognitive tasks that may otherwise go unnoticed by the patients' current system of care.

Large data sets from multiple patients can likewise be analyzed to better understand larger trends in research populations. The sphere can be used in the home to continue care initiated in the clinical environment and as therapeutic means for traumatic brain injury (TBI) patients. By analyzing and utilizing data from the sphere during in-home use, therapists and doctors can learn from patients' home care habits and engagement with their therapies and with their personal care-givers. In a musical context, the recorded data might be played back, mimicking the sonic implications of the gestures of the user during a performance. These performative musical gestures could be re-mapped during the data playback phase, where the recorded data, now might control entirely different musical sounds or even accompanying lights or motors, for example.

Figure 15:
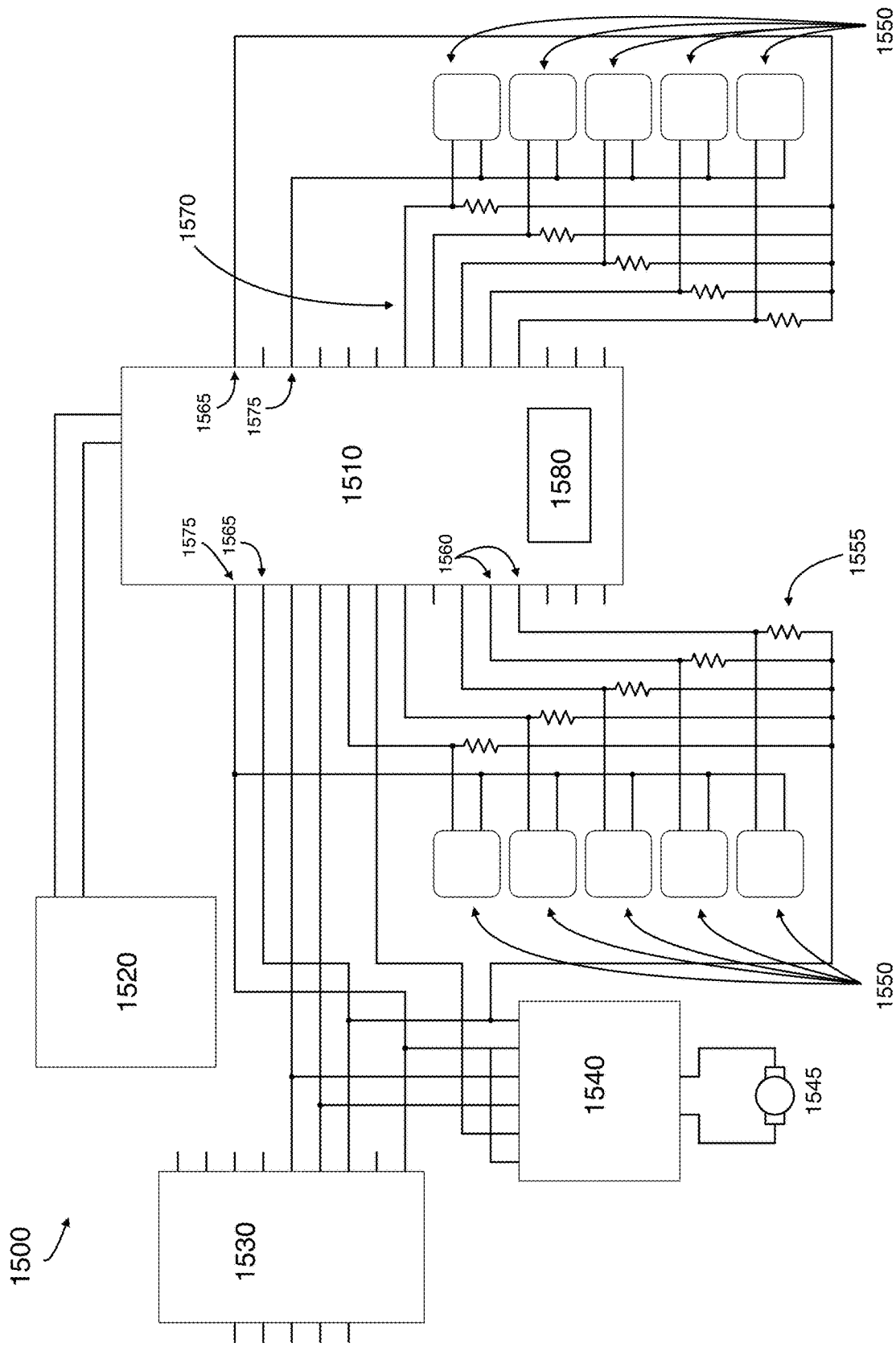
FIG. 15 illustrates a circuit diagram of an exemplary core according to one embodiment of the invention.

FIG. 15 illustrates the electrical components and circuit 1500 of a core 350 according to one embodiment of the invention. In this embodiment, the core 350 includes a central processor 1510. The central processor 1510 includes a sensor microprocessor, Bluetooth module 1580; and components that are electrically coupled to the sensors 1550, battery 1520, haptics 1540, and other electrical devices. In this embodiment, central processor 1510 is connected to battery 1520 which supplies power to central processor and other components of the core 350. Central processor 1510 is also connected to accelerometer/gyroscope/magnetometer (IMU) 1530 through input and output connections, which may include connectors and pins. In one embodiment, the central processor 1510 is connected to a haptic motor driver 1540, which is coupled to a haptic motor 1545. The haptic motor driver 1540 receives input from the central processor 1510 and can activate haptic motor 1545 based on feedback from the sensors, including the force sensors 1550 and IMU 1530. As discussed herein, the IMU 1530 measures the acceleration, spin, tilt and position of the sensorized sphere in three dimensional space. The values of IMU can be used to calibrate the ball and set a baseline threshold of "0", or any other value that is programmed to correspond to the initial starting, or "ready" state of the sensorized sphere; all before the user interacts with the ball to trigger input by the sensors and IMU. In this embodiment, there are ten force sensors 1550 which correspond to each digit of a human hand. Force sensors 1550 are electrically connected to a central processor through connectors 1560 and electrical connections 1570. In one embodiment, the circuit includes resistors 1555 (10*k* ohm) between force sensors 1550 and central processor 1510. The lowering of resistance by sensor activation modulates electrical input into the central processor, and therefore detects changes in the electrical current and measured value of the output. Pins 1560 correspond to the various sensor input pins on central processor 1510. Pins 1565 corresponds to the ground necessary to complete the circuit. Pin 1575 corresponds to the power connection to the force sensors 1550. In this embodiment, central processor 1510 includes a Bluetooth module 1580 which serves as a transceiver, transmitter, or receiver. In one embodiment, the Bluetooth module transmits RF signals to receiver 620 in computing device 600.

Figure 16:
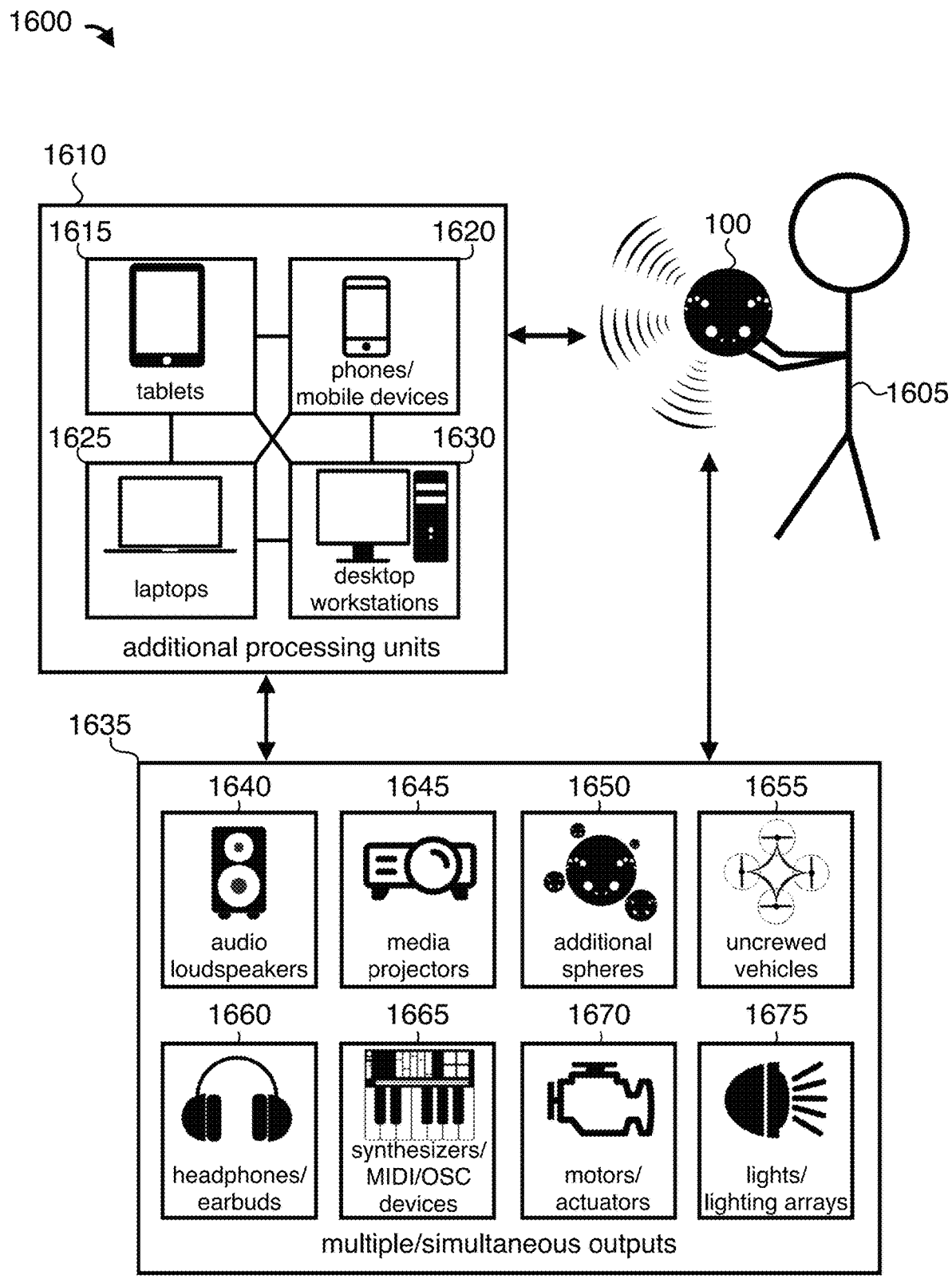
FIG. 16 illustrates an exemplary system embodiment of a sensorized sphere communicating with computer devices and peripheral devices and systems.

FIG. 16 depicts various embodiments of computerized systems and devices 1600 connected to a sensorized sphere. The sensorized sphere may communicate to additional processors or directly to multiple and/or simultaneous outputs. These outputs may be enabled to receive and process data onboard, as modular auxiliary devices. The sphere may communicate directly with additional spheres to produce onboard outputs such as through haptic motors, speakers, lights, and other onboard outputs. The sphere may send and receive data directly to one or more outputs (1635). In situations which benefit from more robust processing (more complex networking, more memory or media storage, and more integration of outputs), additional processing units may be employed. In one embodiment, the user's gestures are captured and transmitted to a mobile device which is connected to a pair of headphones as an output. In one embodiment, the sphere captures and transmits data from user gestures to a desktop workstation which outputs simultaneously to loudspeakers, projectors, a lighting system, and motors to create a multimedia performance where distinct mappings create an integrated set of outputs. In one embodiment the sphere controls a drone, while receiving live video feed from the drone's camera, displayed on the surface of the sphere. As shown here, user 1605 has grasped a sensorized sphere 100 which includes 10 force sensors and some binary modifier buttons between the thumb sensors. In this embodiment, the user is able to interact with the sphere using one or both hands to activate one or more sensors that are configured in spatial proximity to each digit of the human hand. In one embodiment, the sensorized sphere wirelessly communicates with devices 1610, which may include tablet computers 1615, phone and mobile devices 1620, laptops 1625, and desktop workstations 1630. As discussed herein, each of the computerized devices in 1610 may be programmed with software designed to receive, process, and display the data emanating from each of the sensors, IMUs, or binary modifiers included in sensorized sphere 100. As shown in FIG. 16, sensorized sphere 100 or computing devices 1610 may also be connected to other peripheral devices 1635 to render interactive uses and displays. In one embodiment, such devices may include audio speakers 1640, media projectors 1645, additional spheres 1650, uncrewed vehicles 1655 (such as drones), headphones or earbuds 1660, synthesizers or MIDI/OSC-enabled devices 1665, motor or actuators 1670, and lights or lighting arrays 1675. It is contemplated that the sensorized sphere, through different gestures, can control a variety of different devices and outputs. For example, each of the peripheral devices 1635 may have Bluetooth or other RF processing chips that can connect directly to the sensorized sphere, or through a computer device as shown in devices 1610.

Figure 17:
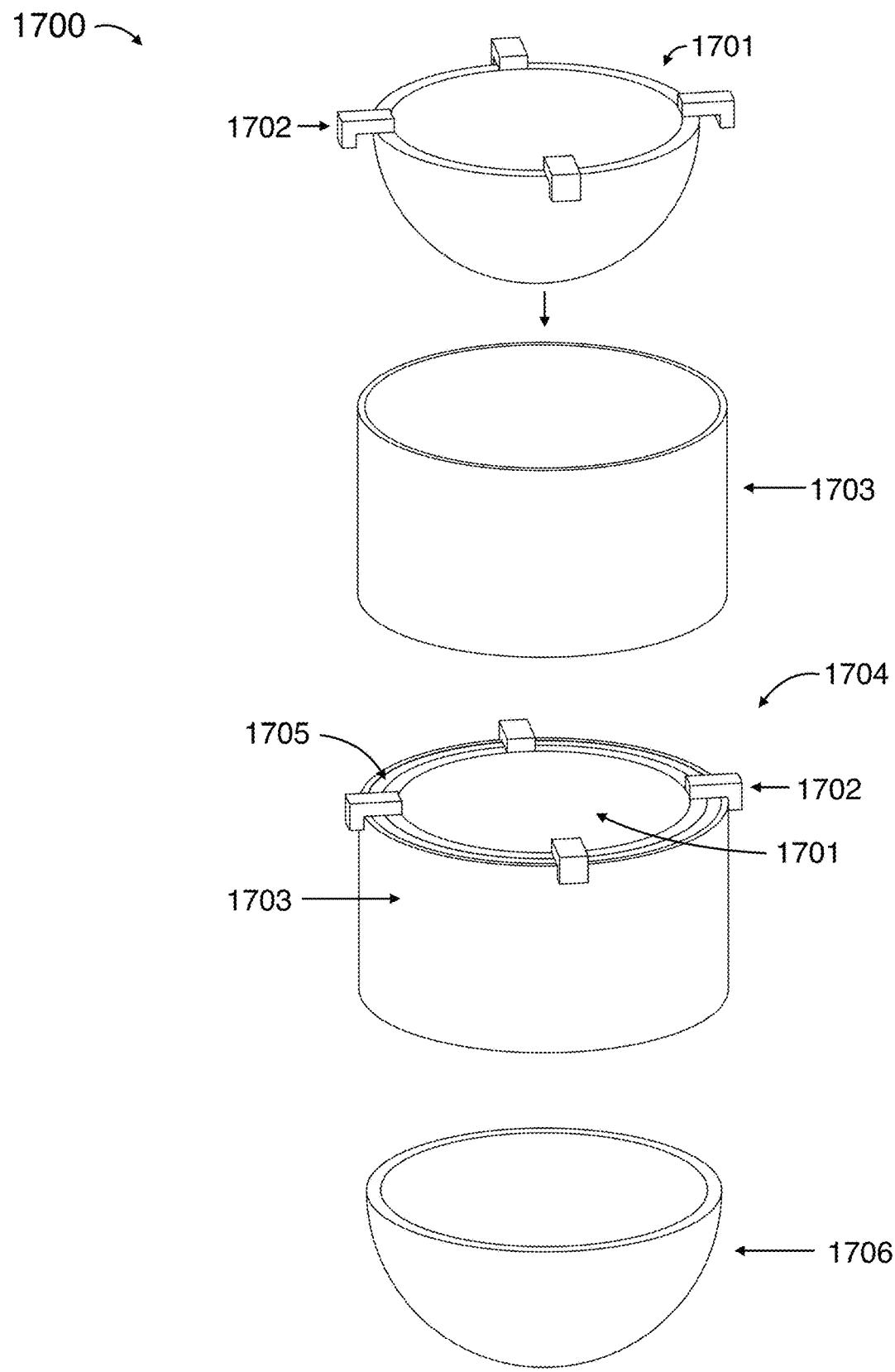
FIG. 17 depicts embodiments of mold apparatuses and methods for making a silicone layer for a hemisphere of a sensorized sphere.
Figure 18:
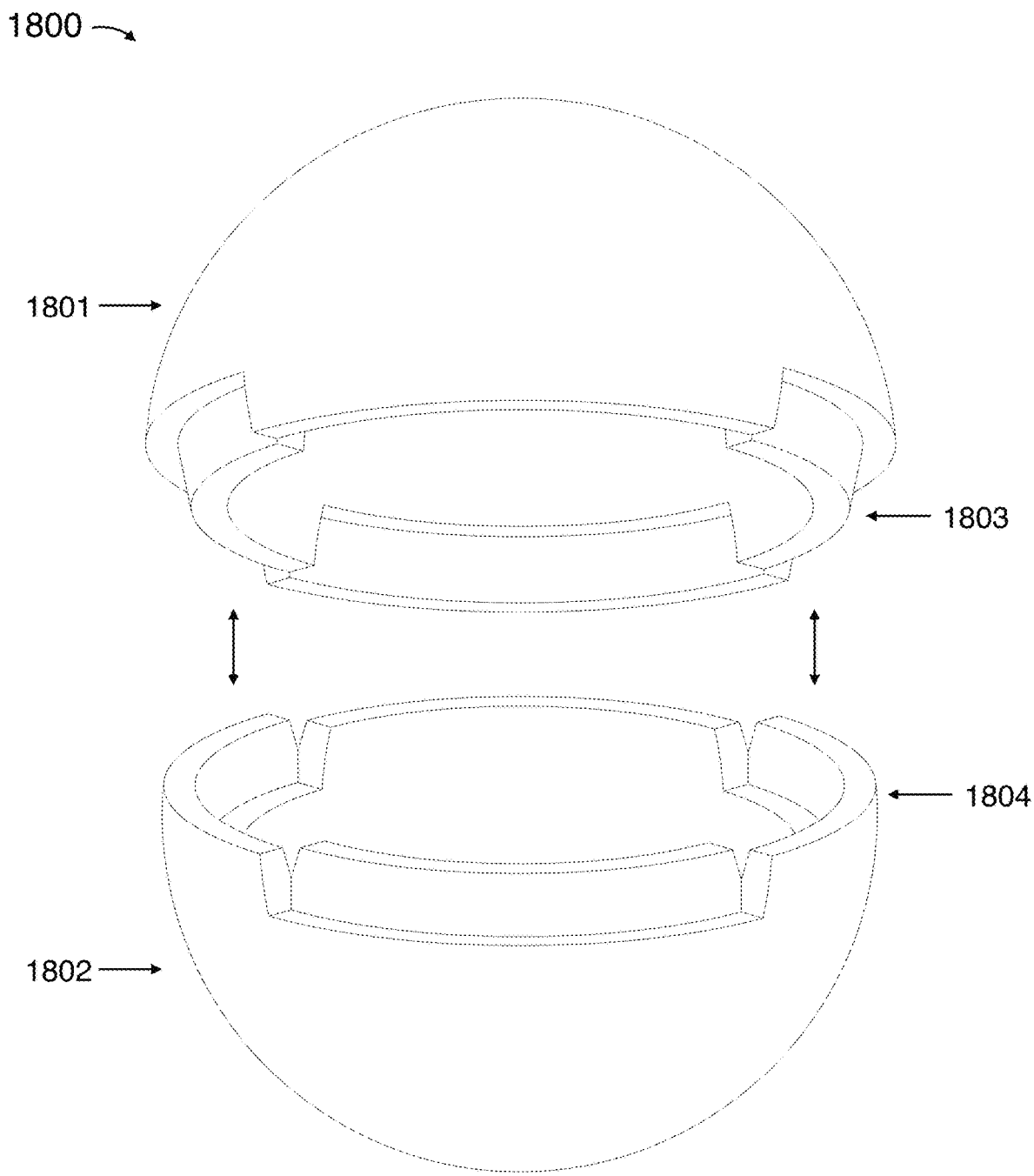
FIG. 18 depicts hemisphere apparatus embodiments and methods for creating a spherical core for a sensorized sphere.

FIG. 17 represents an apparatus and method for creating an outer shell for the core or inner spherical component of a sensorized sphere according to one embodiment. The inner sphere (or core) is shown in FIG. 18. The apparatus and method allow for creating silicone, rubber or polymer shells to form compressive layers to surround the core of the sensorized sphere. 1700 depicts the mold components and process for creating a silicone, rubber or polymer shell. In one embodiment, mold parts are 3D-printed using thermoplastics, PLA or any other suitable 3D printing materials. The mold has two components 1701 and 1703. 1701 is a hemisphere with placement tabs 1702. Mold component 1703 consists of an inner hemispherical concavity that allows for a spaced apart relationship between hemisphere 1701 and the concave inner surface of mold component 1703. Therefore, the diameter of hemispherical concavity of mold 1703 is greater than the diameter of hemisphere 1701. The four tabs 1702 of hemisphere 1701 form L shaped clasps that fit the outer rim of mold 1703. When hemisphere 1701 is placed in mold 1703 the tabs may lock into place and create a spaced apart section 1705 which is the difference in diameter between 1701 and 1703. Once mold parts 1701 and 1703 are connected by tabs 1702, a mold 1704 is formed. The tabs 1702 ensure that hemisphere mold 1701 fits uniformly in the concave space of mold 1703 such that a hemispherical space 1705 is created for pouring silicone or any other suitable substance. Silicone is then poured into space 1705 and sets in space 1705 to form a uniform hemispherical shell. After the silicone cures, mold 1701 is removed from mold 1703 by unclasping tabs 1702. The result is cured silicone shell 1706 which is removed from the hemispherical concavity of mold 1703. The cured silicone shell may also be removed from the hemispherical surface of mold 1701.

FIG. 18 depicts an apparatus 1800 of a 3D printed core according to one embodiment. The core includes hemispheres 1801 and 1802. The hemispheres are identical mirror image components designed to provide symmetry and balance to the sphere. Because each hemisphere is identical, a single mold or design drawing can be used to manufacture or print each hemisphere. Each hemisphere 1801 and 1802 has an inner rim 1803 and an outer rim 1804. The inner rim 1803 meets the outer rim 1804 when the hemispheres are joined. A seamless connection is made when the inner and outer rims of the hemispheres meet to form a complete sphere. Such a mechanism allows the user of the sphere to quickly and easily open up the core by grasping the hemisphere 1801 or 1802 and lifting or twisting the hemisphere to disconnect one hemisphere 1801 from the other hemisphere 1802. This allows the user to open the core to access the electrical components, batteries and microprocessors of the core. In one embodiment, the outer rim 1804 of the hemisphere has a male locking component which meets a female part of the inner rim 1803 of the other hemisphere, such that when a user combines the two hemispheres and twists one of the hemispheres, the two hemispheres are locked by the male and female parts coming together.

The various computerized aspects of a computing device described in connection with the disclosure herein may be implemented or performed with a processor shown as CPU, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor may be a microprocessor, but in the alternative, the processor may be any conventional processor, controller, or microcontroller. A processor may also be implemented as a combination of computing devices, e.g., a combination of a DSP and a microprocessor, a plurality of microprocessors, one or more microprocessors in conjunction with a DSP core, or any other such configuration.

At least some aspects of the methods described herein may be embodied in programming. Program aspects of the technology may be thought of as "products" or "articles of manufacture" typically in the form of executable code and/or associated data that is carried on, embodied in, or physically stored on a type of machine-readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

Those of skill would further appreciate that the various computer instructions or methods in connection with the disclosure herein may be implemented as electronic hardware, computer software, or combinations of both. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

All or portions of the software may at times be communicated through a network such as the Internet or various other telecommunication networks. Such communications, for example, may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Those skilled in the art will recognize that the present teachings are amenable to a variety of modifications and/or enhancements. For example, although the implementation of various components described above may be embodied in a hardware device, it can also be implemented as a software only solution, e.g., an installation on an existing server. In addition, data drive dynamic logging system and its components as disclosed herein can be implemented as a firmware, firmware/software combination, firmware/hardware combination, or a hardware/firmware/software combination.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

The invention claimed is:

1. A method of generating musical outputs from a spherical input and output device, comprising the steps of:
    tossing said device against a surface of an object to generate a return movement; activating a sensor embedded under a compressive material of said device to generate a force signal corresponding to the impact of said device against said surface;
    activating an inertial measurement unit sensor to generate an inertial measurement unit signal corresponding to the acceleration, velocity or spin of said return movement;
    processing said force signal to generate force data;
    processing said inertial measurement unit signal to generate inertial measurement data;
    transmitting said force data and said inertial measurement data to a receiving device electrically coupled to the spherical input and output device;
    translating said force data and said inertial measurement unit data to generate a musical output corresponding to the force and one of acceleration, velocity or rotation of the return movement.

2. The method of claim 1 wherein force data and Inertial Measurement Unit data is translated into a data output in the format of at least one of Musical Instrument Digital Interface (MIDI) data or OSC (Open Sound Control) data.

3. The method of claim 1, further including an algorithm for translating the force data to generate an audio output, wherein the intensity of the audio output is based on the amplitude of the force signal.

4. The method of claim 1, further including an algorithm for translating the rotation of said device to generate audio output modified by at least one of sample playback speed, filter sweeps, frequency, or panning.

5. The method of claim 1, further including an algorithm for translating combinations of Inertial Measurement Unit data, including data representing an altitude of said device or other calculations of position, orientation, or movement in three-dimensional space of said device into modifications of said musical output based at least one of timbre, tone, rhythm, melody, frequency, or pitch.

6. The method of claim 1, further including an algorithm for translating a temporal interval between successive impacts of said device against said surface wherein the musical output is timed for playback from a set of predetermined options based on a series of temporal interval thresholds.

7. The method of claim 1, further including an algorithm for translating said force data to generate a lighting effect on said device based on the intensity of impact of said device against said surface.

8. The method of claim 1, further including an algorithm for processing the intensity of said force signal to generate force data that is further translated into a lighting output wherein colors of said lighting output based on the intensity of impact of said device against said surface.

9. A spherical input and output device for capturing a return movement from tossing said device against a surface, said device comprising:
- a compressive outer shell for absorbing the force of said device against said surface;
- a protected inner core with a power source for powering electrical components comprising:
- a sensor for capturing a force of impact of said device against said surface to generate force signals;
- an inertial measurement unit sensor for measuring the return movement of said device to generate inertial measurement signals corresponding to acceleration, velocity or spherical rotation of said device;
- a microprocessor for processing force signals and inertial measurement signals for generating force data and inertial measurement unit data;
- a transceiver for transmitting force data and inertial measurement unit data to a receiving device electrically coupled to the spherical input and output device,
- said receiving device comprising:
- an algorithm for translating said force data and said inertial measurement unit data to generate a musical output corresponding to the force and one of acceleration, velocity or spin of the return movement.

10. The device of claim 9 wherein said device includes an outer protective material made of at least one of rubber, silicone, plastic, glass, wood, fabric, or a synthetic polymer.

11. The device of claim 10 wherein the inner core of said device is protected, and suspended through symmetrical distribution of weight in the center of the device.

12. The device of claim 10 wherein the outer shell of said device is constructed of a synthetic polymer or a combination synthetic polymers to facilitate the return movement of the device.

13. The device of claim 10 which includes at least one video camera embedded on the outer shell.

14. The device of claim 10 wherein the outer shell of said device is constructed of a series of individual panels arranged in such a way as to form a spherical shaped covering.

15. The device of claim 10 further comprising at least one Light Emitting Diode (LED) or other light emitting elements.

16. The device of claim 10 further comprising at least one haptic motor to provide the user with tactile feedback.

17. The device of claim 10 further comprising at least one video display screen on the outer shell of said device.

18. The device of claim 10 wherein the outer shell is constructed of a transparent or translucent material optimized for light diffusion through the outer shell.

19. The device of claim 10 further comprising a tactile matrix sensor array on said outer shell optimized to detect touch and impact on the surface of said device, such that a user can hold or grip the device from any direction and their fingertips will land on at least one tactile element of said tactile matrix.

\* \* \* \* \*